United States Patent
Davies et al.

(10) Patent No.: US 7,528,296 B2
(45) Date of Patent: May 5, 2009

(54) GENERATION OF PLANTS WITH ALTERED OIL CONTENT

(75) Inventors: John Davies, Portland, OR (US); Sandra Peters, Portland, OR (US); Hein Tsoeng Ng, Beaverton, OR (US)

(73) Assignee: Agrinomics, LLC, Portland, OR (US)

( * ) Notice: Subject to any disclaimer, the term of this patent is extended or adjusted under 35 U.S.C. 154(b) by 98 days.

(21) Appl. No.: 11/597,026

(22) PCT Filed: May 26, 2005

(86) PCT No.: PCT/US2005/018908

§ 371 (c)(1),
(2), (4) Date: Nov. 17, 2006

(87) PCT Pub. No.: WO2005/118819

PCT Pub. Date: Dec. 15, 2005

(65) Prior Publication Data

US 2007/0245433 A1    Oct. 18, 2007

Related U.S. Application Data

(60) Provisional application No. 60/575,560, filed on May 28, 2004.

(51) Int. Cl.
*A01H 5/00*    (2006.01)
*C12N 15/82*   (2006.01)
*A21D 2/00*    (2006.01)
*C12N 5/14*    (2006.01)

(52) U.S. Cl. .................. 800/298; 435/468; 435/419; 800/312; 800/314; 800/320; 800/320.1; 426/622

(58) Field of Classification Search ................ None
See application file for complete search history.

(56) References Cited

U.S. PATENT DOCUMENTS

| | | | |
|---|---|---|---|
| 5,639,790 A | 6/1997 | Voelker et al. |
| 5,704,160 A | 1/1998 | Bergquist et al. |
| 6,229,033 B1 | 5/2001 | Knowlton |
| 6,248,939 B1 | 6/2001 | Leto et al. |

FOREIGN PATENT DOCUMENTS

| | | |
|---|---|---|
| WO | WO99/58654 | 11/1999 |
| WO | WO01/083697 | 11/2001 |
| WO | WO03/079766 | 10/2003 |

OTHER PUBLICATIONS

Yamagata et al. (Biosci. Biotechnol. Biochem.64:1947-1957, 2000).*
Zou et al. (The Plant Cell, 9:909-923, 1997).*
Jako et al. (Plant Physiol. 126:861-874, 2001).*
Keskin et al. (Protein Science, 13:1043-1055, 2004.*
Thornton et al. (Nature structural Biology, structural genomics supplement, Nov. 2000).*
Guo et al. (PNAS, 101: 9205-9210, 2004).*
Wells, (Biochemistry 29:8509-8517, 1990).*
Ngo et al., (The Protein Folding Problem and Tertiary Structure Prediction, K. Merz., and S. Le Grand (eds.) pp. 492-495, 1994).*
Doerks et al., (TIG, 14:248-250, 1998).*
Smith et al. (Nature Biotechnology, 15:1222-1223, 1997).*
Bork et al. (TIG, 12:425-427, 1996).*
Anoop et al., "Modulation of citrate metabolism alters aluminum tolerance in yeast and transgenic canola overexpressing a mitochondrial citrate synthase," *Plant Physiol.*, 132:2205-2217, 2003.
Beisson et al., "*Arabidopsis* genes involved in acyl lipid metabolism. A 2003 census of the candidates, a study of the distribution of expressed sequence tags in organs, and a web-based database," *Plant Physiol.*, 132:681-697, 2003.
Bert et al., "Comparative genetic analysis of quantitative traits in sunflower (*Helianthus annuss* L.). 2. Characterisation of QTL involved in developmental and agronomic traits," *Theor. Appl. Genet.*, 107:181-189, 2003.
Colbert et al., "High-throughput screening for induced point mutations," *Plant Physiol.*, 126(2):480-484, 2001.
DeHesh et al., "Overexpression of 3-ketoacyl-acyl-carrier protein synthase IIIs in plants reduces the rate of lipid synthesis," *Plant Physiol.*, 125:1103-1114, 2001.
Eastmond and Graham, "Re-examining the role of glyoxylate cycle in oilseeds," *Trends Plant Sci.*, 6(2):72-77, 2001.
Eccleston and Ohlrogge, "Expressions of lauroyl-acyl carrier protein thioesterase in *Brassica napus* seeds induces pathways for both fatty acid oxidation and biosynthesis and implies a set point for triacylglycerol accumulation," *Plant Cell.* 10:613-621, 1998.
Fatland et al., "Molecular biology of cytosolic acetyl-CoA generation," *Biochem. Soc. Trans.*, 28(6):593-595, 2000.
Fatland et al., "Reverse genetic characterization of cytosolic acetyl-CoA generation by ATP-citrate lyase in *Arabidopsis*," *Plant Cell*, 17:182-203, 2005.
Feldmann et al., "A Dwarf Mutant of *Arabidopsis* Generated by T-DNA Insertion Mutagenesis," *Science*, 243 (4896):1351-1354, 1989.
Focks and Benning, "*wrinkled1*: A novel, low-seed-oil mutant of *Arabidopsis* with a deficiency in the seed-specific regulation of carbohydrate metabolism," *Plant Physiol.*, 118:91-101, 1998.
Girke et al., "Microarray analysis of developing *Arabidopsis* seeds," *Plant Physiol.*, 124:1570-1581, 2000.
Jako et al., "Seed-specific over-expression of an *Arabidopsis* cDNA encoding a diacylglycerol acyltransferase enhances seed oil content and seed weight," *Plant Physiol.*, 126(2):861-874, 2001.
James and Dooner, "Isolation of EMS-induced mutants in *Arabidopsis* altered in seed fatty acid composition," *Theor. Appl. Genet.*, 80(2):241-245, 1990.

(Continued)

Primary Examiner—Phuong T Bui
Assistant Examiner—Vinod Kumar
(74) Attorney, Agent, or Firm—Klarquist Sparkman, LLP

(57) ABSTRACT

The present invention is directed to plants that display an altered oil content phenotype due to altered expression of a HIO1004 nucleic acid. The invention is further directed to methods of generating plants with an altered oil content phenotype.

9 Claims, No Drawings

OTHER PUBLICATIONS

Katavic et al., "Alteration of seed fatty acid composition by an ethyl methanesulfonate-induced mutation in *Arabidopsis thaliana* affecting diacylglycerol acyltransferase activity," *Plant Physiol.*, 108:399-409, 1995.

Katavic et al., "Utility of the *Arabidopsis FAE1* and yeast *SLC1-1* genes for improvements in erucic acid and oil content in rapeseed," *Biochem Soc. Trans.*, 28(6):935-937, 2000.

Larson et al., "Acyl CoA profiles of transgenic plants that accumulate medium-chain fatty acids indicate inefficient storage lipid synthesis in developing oilseeds," *Plant J.*, 32:519-527, 2002.

Lemieux et al., "Mutants of *Arabidopsis* with alterations in seed lipid fatty acid composition," *Theor. Appl. Genet.*, 80(2):234-240, 1990.

Lin et al., "The Pex16p homolog SSE1 and storage organelle formation in *Arabidopsis* seeds," *Science.* 284:328-330, 1999.

Lionneton et al., "Development of an AFLP-based linkage map and localization of QTLs for seed fatty acid content in condiment mustard (*Brassica juncea*)," *Genome*, 45(6):1203-1215, 2002.

Liu and Butow, "A transcriptional switch in the expression of yeast tricarboxylic acid cycle genes in response to a reduction or loss of respiratory function," *Mol. Cell. Biol.*, 19:6720-6728, 1999.

McCallum et al., "Targeted screening for induced mutations," *Nat. Biotechnol.*, 18(4):455-457, 2000.

Mekhedov et al., "Toward a functional catalog of the plant genome. A survey of genes for lipid biosynthesis," *Plant Physiol.*, 122:389-401, 2000.

Moire et al., "Impact of unusual fatty acid synthesis on futile cycling through β-oxidation and on gene expression in transgenic plants," *Plant Physiol.*, 134:432-442, 2004.

Neuhaus and Emes, "Nonphotosynthetic Metabolism In Plastids," *Annu. Rev. Plant Physiol. Plant Mol. Biol.*, 51:111-140, 2000.

O'Hara et al., "Fatty acid and lipid biosynthetic genes are expressed at constant molar ratios but different absolute levels during embryogenesis," *Plant Physiol.*, 129:310-320, 2002.

Okuley et al., "*Arabidopsis FAD2* Gene Encodes the Enzyme That Is Essential for Polyunsaturated Lipid Synthesis," *Plant Cell*, 6:147-158, 1994.

Pritchard et al., "Germination and storage reserve mobilization are regulated independently in *Arabidopsis*," *Plant J.*, 31(5):639-647, 2002.

Rangasamy and Ratledge, "Compartmentation of ATP:Citrate lyase in plants," *Plant Physiol.*, 122:1225-1230, 2000.

Rangasamy and Ratledge, "Genetic enhancement of fatty acid synthesis by targeting rat liver ATP:citrate lyase into plastids of tobacco," *Plant Physiol.*, 122:1231-1238, 2000.

Ratledge et al, "Correlation of ATP/citrate lyase activity with lipid accumulation in developing seeds of *Brassica napus* L., " *Lipids*, 32(1):7-12, 1997.

Rawsthorne, S., "Carbon flux and fatty acid synthesis in plants," *Prog Lipid Res.*, 41:182-196, 2002.

Ruuska et al., "Contrapuntal networks of gene expression during *Arabidopsis* seed filling," *Plant Cell*, 14:1191-1206, 2002.

Rylott et al., "Co-ordinate regulation of genes involved in storage lipid mobilization in *Arabidopsis thaliana*," *Biochem Soc. Trans.*, 29:283-287, 2001.

Schnarrenberger and Martin, "Evolution of the enzymes of the citric acid cycle and the glyoxylate cycle of higher plants, A case study of endosymbiotic gene transfer," *Eur. J. Biochem.*, 269:868-883, 2002.

Schnurr et al. "Characterization of an acyl-CoA synthetase from *Arabidopsis thaliana*," *Biochem Soc.Trans.*, 28(6):957-958, 2000.

Shockey et al., "Characterization of the AMP-binding protein gene family in *Arabidopsis thaliana*: will the real acyl-CoA synthetases please stand up?" *Biochem Soc. Trans.*, 28(6):955-957, 2000.

Thelen et al., "Biotin carboxyl carrier protein isoforms in *Brassicaceae* oilseeds," *Biochem. Soc. Trans.*, 28(6);595-598, 2000.

Wada et al., "Role of a positive regulator of root hair development, Caprice, in *Arabidopsis* root epidermal cell differentiation," *Development*, 129(23):5409-5419, 2002.

White et al., "A new set of *Arabidopsis* expressed sequence tags from developing seeds. The metabolic pathway from carbohydrates to seed oil," *Plant Physiol.*, 124:1582-1594, 2000.

Yadav et al., "Cloning of higher plant omega-3 fatty acid desaturases," *Plant Physiol.*, 103(2):467-476, 1993.

EmbL Database Accession No. AY133682, Aug. 12, 2002, 2 pages.

Uniprot Database Accession No. Q8L7I2, Oct. 1, 2002, 1 page.

* cited by examiner

GENERATION OF PLANTS WITH ALTERED OIL CONTENT

REFERENCE TO RELATED APPLICATIONS

This is the §371 U.S. National Stage of International Application No. PCT/US2005/018908, filed May 26, 2005, which was published in English under PCT Article 21(2), which in turn claims the benefit of U.S. Provisional Application No. 60/575,560, filed May 28, 2004, the contents of both of which are hereby incorporated by reference.

BACKGROUND OF THE INVENTION

The ability to manipulate the composition of crop seeds, particularly the content and composition of seed oils, has important applications in the agricultural industries, relating both to processed food oils and to oils for animal feeding. Seeds of agricultural crops contain a variety of valuable constituents, including oil, protein and starch. Industrial processing can separate some or all of these constituents for individual sale in specific applications. For instance, nearly 60% of the U.S. soybean crop is crushed by the soy processing industry. Soy processing yields purified oil, which is sold at high value, while the remainder is sold principally for lower value livestock feed (US Soybean Board, 2001 Soy Stats). Canola seed is crushed to produce oil and the co-product canola meal (Canola Council of Canada). Nearly 20% of the 1999/2000 US corn crop was industrially refined, primarily for production of starch, ethanol and oil (Corn Refiners Association). Thus, it is often desirable to maximize oil content of seeds. For instance, for processed oilseeds such as soy and canola, increasing the absolute oil content of the seed will increase the value of such grains. For processed corn it may be desired to either increase or decrease oil content, depending on utilization of other major constituents. Decreasing oil may improve the quality of isolated starch by reducing undesired flavors associated with oil oxidation. Alternatively, in ethanol production, where flavor is unimportant, increasing oil content may increase overall value. In many fed grains, such as corn and wheat, it is desirable to increase seed oil content, because oil has higher energy content than other seed constituents such as carbohydrate. Oilseed processing, like most grain processing businesses, is a capital-intensive business; thus small shifts in the distribution of products from the low valued components to the high value oil component can have substantial economic impacts for grain processors.

Biotechnological manipulation of oils can provide compositional alteration and improvement of oil yield. Compositional alterations include high oleic soybean and corn oil (U.S. Pat. Nos. 6,229,033 and 6,248,939), and laurate-containing seeds (U.S. Pat. No. 5,639,790), among others. Work in compositional alteration has predominantly focused on processed oilseeds but has been readily extendable to non-oilseed crops, including corn. While there is considerable interest in increasing oil content, the only currently practiced biotechnology in this area is High-Oil Corn (HOC) technology (DuPont, U.S. Pat. No. 5,704,160). HOC employs high oil pollinators developed by classical selection breeding along with elite (male-sterile) hybrid females in a production system referred to as TopCross. The TopCross High Oil system raises harvested grain oil content in maize from about 3.5% to about 7%, improving the energy content of the grain.

While it has been fruitful, the HOC production system has inherent limitations. First, the system of having a low percentage of pollinators responsible for an entire field's seed set contains inherent risks, particularly in drought years. Second, oil contents in current HOC fields have plateaued at about 9% oil. Finally, high-oil corn is not primarily a biochemical change, but rather an anatomical mutant (increased embryo size) that has the indirect result of increasing oil content. For these reasons, an alternative high oil strategy, particularly one that derives from an altered biochemical output, would be especially valuable.

The most obvious target crops for the processed oil market are soy and rapeseed, and a large body of commercial work (e.g., U.S. Pat. No. 5,952,544; PCT application WO9411516) demonstrates that *Arabidopsis* is an excellent model for oil metabolism in these crops. Biochemical screens of seed oil composition have identified *Arabidopsis* genes for many critical biosynthetic enzymes and have led to identification of agronomically important gene orthologs. For instance, screens using chemically mutagenized populations have identified lipid mutants whose seeds display altered fatty acid composition (Lemieux et al., 1990; James and Dooner, 1990). T-DNA mutagenesis screens (Feldmann et al., 1989) that detected altered fatty acid composition identified the omega 3 desaturase (FAD3) and delta-12 desaturase (FAD2) genes (U.S. Pat. No. 5,952,544; Yadav et al., 1993; Okuley et al., 1994). A screen which focused on oil content rather than oil quality, analyzed chemically-induced mutants for wrinkled seeds or altered seed density, from which altered seed oil content was inferred (Focks and Benning, 1998). Another screen, designed to identify enzymes involved in production of very long chain fatty acids, identified a mutation in the gene encoding a diacylglycerol acyltransferase (DGAT) as being responsible for reduced triacyl glycerol accumulation in seeds (Katavic V et al, 1995). It was further shown that seed-specific over-expression of the DGAT cDNA was associated with increased seed oil content (Jako et al., 2001).

Activation tagging in plants refers to a method of generating random mutations by insertion of a heterologous nucleic acid construct comprising regulatory sequences (e.g., an enhancer) into a plant genome. The regulatory sequences can act to enhance transcription of one or more native plant genes; accordingly, activation tagging is a fruitful method for generating gain-of-function, generally dominant mutants (see, e.g., Hayashi et al., 1992; Weigel D et al. 2000). The inserted construct provides a molecular tag for rapid identification of the native plant whose mis-expression causes the mutant phenotype. Activation tagging may also cause loss-of-function phenotypes. The insertion may result in disruption of a native plant gene, in which case the phenotype is generally recessive.

Activation tagging has been used in various species, including tobacco and *Arabidopsis*, to identify many different kinds of mutant phenotypes and the genes associated with these phenotypes (Wilson et al., 1996, Schaffer et al., 1998, Fridborg et al., 1999; Kardailsky et al., 1999; Christensen S et al., 1998).

SUMMARY OF THE INVENTION

The invention provides a transgenic plant having a high oil phenotype. The transgenic plant comprises a transformation vector comprising a nucleotide sequence that encodes or is complementary to a sequence that encodes a HIO1004 polypeptide. In preferred embodiments, the transgenic plant is selected from the group consisting of rapeseed, soy, corn, sunflower, cotton, cocoa, safflower, oil palm, coconut palm, flax, castor and peanut. The invention further provides a method of producing oil comprising growing the transgenic plant and recovering oil from said plant.

The invention also provides a transgenic plant cell having a high oil phenotype. The transgenic plant cell comprises a transformation vector comprising a nucleotide sequence that encodes or is complementary to a sequence that encodes a High Oil (hereinafter "HIO1004") polypeptide. In preferred embodiments, the transgenic plant cell is selected from the group consisting of rapeseed, soy, corn, sunflower, cotton, cocoa, safflower, oil palm, coconut palm, flax, castor and peanut. In other embodiments, the plant cell is a seed, pollen, propagule, or embryo cell. The invention further provides feed, meal, grain, food, or seed comprising a nucleic acid sequence that encodes a HIO1004 polypeptide. The invention also provides feed, meal, grain, food, or seed comprising the HIO1004 polypeptide, or an ortholog thereof.

The transgenic plant of the invention is produced by a method that comprises introducing into progenitor cells of the plant a plant transformation vector comprising a nucleotide sequence that encodes or is complementary to a sequence that encodes a HIO1004 polypeptide, and growing the transformed progenitor cells to produce a transgenic plant, wherein the HIO1004 polynucleotide sequence is expressed causing the high oil phenotype. The invention further provides plant cells obtained from said transgenic plant.

The present invention also provides a container of over about 10,000, more preferably about 20,000, and even more preferably about 40,000 seeds where over about 10%, more preferably about 25%, more preferably about 50%, and even more preferably about 75% or more preferably about 90% of the seeds are seeds derived from a plant of the present invention.

The present invention also provides a container of over about 10 kg, more preferably about 25 kg, and even more preferably about 50 kg seeds where over about 10%, more preferably about 25%, more preferably about 50%, and even more preferably about 75% or more preferably about 90% of the seeds are seeds derived from a plant of the present invention.

Any of the plants or parts thereof of the present invention may be processed to produce a feed, meal, or oil preparation. A particularly preferred plant part for this purpose is a seed. In a preferred embodiment the feed, meal, or oil preparation is designed for ruminant animals. Methods to produce feed, meal, and oil preparations are known in the art. See, for example, U.S. Pat. Nos. 4,957,748; 5,100,679; 5,219,596; 5,936,069; 6,005,076; 6,146,669; and 6,156,227. The meal of the present invention may be blended with other meals. In a preferred embodiment, the meal produced from plants of the present invention or generated by a method of the present invention constitutes greater than about 0.5%, about 1%, about 5%, about 10%, about 25%, about 50%, about 75%, or about 90% by volume or weight of the meal component of any product. In another embodiment, the meal preparation may be blended and can constitute greater than about 10%, about 25%, about 35%, about 50%, or about 75% of the blend by volume.

DETAILED DESCRIPTION OF THE INVENTION

Definitions

Unless otherwise indicated, all technical and scientific terms used herein have the same meaning as they would to one skilled in the art of the present invention. Practitioners are particularly directed to Sambrook et al., 1989, and Ausubel F M et al., 1993, for definitions and terms of the art. It is to be understood that this invention is not limited to the particular methodology, protocols, and reagents described, as these may vary.

As used herein, the term "vector" refers to a nucleic acid construct designed for transfer between different host cells. An "expression vector" refers to a vector that has the ability to incorporate and express heterologous DNA fragments in a foreign cell. Many prokaryotic and eukaryotic expression vectors are commercially available. Selection of appropriate expression vectors is within the knowledge of those having skill in the art.

A "heterologous" nucleic acid construct or sequence has a portion of the sequence that is not native to the plant cell in which it is expressed. Heterologous, with respect to a control sequence refers to a control sequence (i.e. promoter or enhancer) that does not function in nature to regulate the same gene the expression of which it is currently regulating. Generally, heterologous nucleic acid sequences are not endogenous to the cell or part of the genome in which they are present, and have been added to the cell, by infection, transfection, microinjection, electroporation, or the like. A "heterologous" nucleic acid construct may contain a control sequence/DNA coding sequence combination that is the same as, or different from a control sequence/DNA coding sequence combination found in the native plant.

As used herein, the term "gene" means the segment of DNA involved in producing a polypeptide chain, which may or may not include regions preceding and following the coding region, e.g. 5' untranslated (5'UTR) or "leader" sequences and 3'UTR or "trailer" sequences, as well as intervening sequences (introns) between individual coding segments (exons) and non-transcribed regulatory sequence.

As used herein, "recombinant" includes reference to a cell or vector, that has been modified by the introduction of a heterologous nucleic acid sequence or that the cell is derived from a cell so modified. Thus, for example, recombinant cells express genes that are not found in identical form within the native (non-recombinant) form of the cell or express native genes that are otherwise abnormally expressed, under expressed or not expressed at all as a result of deliberate human intervention.

As used herein, the term "gene expression" refers to the process by which a polypeptide is produced based on the nucleic acid sequence of a gene. The process includes both transcription and translation; accordingly, "expression" may refer to either a polynucleotide or polypeptide sequence, or both. Sometimes, expression of a polynucleotide sequence will not lead to protein translation. "Over-expression" refers to increased expression of a polynucleotide and/or polypeptide sequence relative to its expression in a wild-type (or other reference [e.g., non-transgenic]) plant and may relate to a naturally-occurring or non-naturally occurring sequence. "Ectopic expression" refers to expression at a time, place, and/or increased level that does not naturally occur in the non-altered or wild-type plant. "Under-expression" refers to decreased expression of a polynucleotide and/or polypeptide sequence, generally of an endogenous gene, relative to its expression in a wild-type plant. The terms "mis-expression" and "altered expression" encompass over-expression, under-expression, and ectopic expression.

The term "introduced" in the context of inserting a nucleic acid sequence into a cell, means "transfection", or "transformation" or "transduction" and includes reference to the incorporation of a nucleic acid sequence into a eukaryotic or prokaryotic cell where the nucleic acid sequence may be incorporated into the genome of the cell (for example, chromosome, plasmid, plastid, or mitochondrial DNA), converted into an autonomous replicon, or transiently expressed (for example, transfected mRNA).

As used herein, a "plant cell" refers to any cell derived from a plant, including cells from undifferentiated tissue (e.g., callus) as well as plant seeds, pollen, propagules and embryos.

As used herein, the terms "native" and "wild-type" relative to a given plant trait or phenotype refers to the form in which that trait or phenotype is found in the same variety of plant in nature.

As used herein, the term "modified" regarding a plant trait, refers to a change in the phenotype of a transgenic plant relative to the similar non-transgenic plant. An "interesting phenotype (trait)" with reference to a transgenic plant refers to an observable or measurable phenotype demonstrated by a T1 and/or subsequent generation plant, which is not displayed by the corresponding non-transgenic (i.e., a genotypically similar plant that has been raised or assayed under similar conditions). An interesting phenotype may represent an improvement in the plant or may provide a means to produce improvements in other plants. An "improvement" is a feature that may enhance the utility of a plant species or variety by providing the plant with a unique and/or novel quality. An "altered oil content phenotype" refers to measurable phenotype of a genetically modified plant, where the plant displays a statistically significant increase or decrease in overall oil content (i.e., the percentage of seed mass that is oil), as compared to the similar, but non-modified plant. A high oil phenotype refers to an increase in overall oil content.

As used herein, a "mutant" polynucleotide sequence or gene differs from the corresponding wild type polynucleotide sequence or gene either in terms of sequence or expression, where the difference contributes to a modified plant phenotype or trait. Relative to a plant or plant line, the term "mutant" refers to a plant or plant line which has a modified plant phenotype or trait, where the modified phenotype or trait is associated with the modified expression of a wild type polynucleotide sequence or gene.

As used herein, the term "T1" refers to the generation of plants from the seed of T0 plants. The T1 generation is the first set of transformed plants that can be selected by application of a selection agent, e.g., an antibiotic or herbicide, for which the transgenic plant contains the corresponding resistance gene. The term "T2" refers to the generation of plants by self-fertilization of the flowers of T1 plants, previously selected as being transgenic. T3 plants are generated from T2 plants, etc. As used herein, the "direct progeny" of a given plant derives from the seed (or, sometimes, other tissue) of that plant and is in the immediately subsequent generation; for instance, for a given lineage, a T2 plant is the direct progeny of a T1 plant. The "indirect progeny" of a given plant derives from the seed (or other tissue) of the direct progeny of that plant, or from the seed (or other tissue) of subsequent generations in that lineage; for instance, a T3 plant is the indirect progeny of a T1 plant.

As used herein, the term "plant part" includes any plant organ or tissue, including, without limitation, seeds, embryos, meristematic regions, callus tissue, leaves, roots, shoots, gametophytes, sporophytes, pollen, and microspores. Plant cells can be obtained from any plant organ or tissue and cultures prepared therefrom. The class of plants which can be used in the methods of the present invention is generally as broad as the class of higher plants amenable to transformation techniques, including both monocotyledenous and dicotyledenous plants.

As used herein, "transgenic plant" includes a plant that comprises within its genome a heterologous polynucleotide. The heterologous polynucleotide can be either stably integrated into the genome, or can be extra-chromosomal. Preferably, the polynucleotide of the present invention is stably integrated into the genome such that the polynucleotide is passed on to successive generations. A plant cell, tissue, organ, or plant into which the heterologous polynucleotides have been introduced is considered "transformed", "transfected", or "transgenic". Direct and indirect progeny of transformed plants or plant cells that also contain the heterologous polynucleotide are also considered transgenic.

Various methods for the introduction of a desired polynucleotide sequence encoding the desired protein into plant cells are available and known to those of skill in the art and include, but are not limited to: (1) physical methods such as microinjection, electroporation, and microprojectile mediated delivery (biolistics or gene gun technology); (2) virus mediated delivery methods; and (3) *Agrobacterium*-mediated transformation methods.

The most commonly used methods for transformation of plant cells are the *Agrobacterium*-mediated DNA transfer process and the biolistics or microprojectile bombardment mediated process (i.e., the gene gun). Typically, nuclear transformation is desired but where it is desirable to specifically transform plastids, such as chloroplasts or amyloplasts, plant plastids may be transformed utilizing a microprojectile-mediated delivery of the desired polynucleotide.

*Agrobacterium*-mediated transformation is achieved through the use of a genetically engineered soil bacterium belonging to the genus *Agrobacterium*. A number of wild-type and disarmed strains of *Agrobacterium tumefaciens* and *Agrobacterium rhizogenes* harboring Ti or Ri plasmids can be used for gene transfer into plants. Gene transfer is done via the transfer of a specific DNA known as "T-DNA" that can be genetically engineered to carry any desired piece of DNA into many plant species.

*Agrobacterium*-mediated genetic transformation of plants involves several steps. The first step, in which the virulent *Agrobacterium* and plant cells are first brought into contact with each other, is generally called "inoculation". Following the inoculation, the *Agrobacterium* and plant cells/tissues are permitted to be grown together for a period of several hours to several days or more under conditions suitable for growth and T-DNA transfer. This step is termed "co-culture". Following co-culture and T-DNA delivery, the plant cells are treated with bactericidal or bacteriostatic agents to kill the *Agrobacterium* remaining in contact with the explant and/or in the vessel containing the explant. If this is done in the absence of any selective agents to promote preferential growth of transgenic versus non-transgenic plant cells, then this is typically referred to as the "delay" step. If done in the presence of selective pressure favoring transgenic plant cells, then it is referred to as a "selection" step. When a "delay" is used, it is typically followed by one or more "selection" steps.

With respect to microprojectile bombardment (U.S. Pat. No. 5,550,318 (Adams et al.); U.S. Pat. No. 5,538,880 (Lundquist et. al.), U.S. Pat. No. 5,610,042 (Chang et al.); and PCT Publication WO 95/06128 (Adams et al.); each of which is specifically incorporated herein by reference in its entirety), particles are coated with nucleic acids and delivered into cells by a propelling force. Exemplary particles include those comprised of tungsten, platinum, and preferably, gold.

An illustrative embodiment of a method for delivering DNA into plant cells by acceleration is the Biolistics Particle Delivery System (BioRad, Hercules, Calif.), which can be used to propel particles coated with DNA or cells through a screen, such as a stainless steel or Nytex screen, onto a filter surface covered with monocot plant cells cultured in suspension.

Microprojectile bombardment techniques are widely applicable, and may be used to transform virtually any plant species. Examples of species that have been transformed by microprojectile bombardment include monocot species such as maize (International Publication No. WO 95/06128 (Adams et al.)), barley, wheat (U.S. Pat. No. 5,563,055 (Townsend et al.) incorporated herein by reference in its entirety), rice, oat, rye, sugarcane, and sorghum; as well as a number of dicots including tobacco, soybean (U.S. Pat. No. 5,322,783 (Tomes et al.), incorporated herein by reference in its entirety), sunflower, peanut, cotton, tomato, and legumes in general (U.S. Pat. No. 5,563,055 (Townsend et al.) incorporated herein by reference in its entirety).

To select or score for transformed plant cells regardless of transformation methodology, the DNA introduced into the cell contains a gene that functions in a regenerable plant tissue to produce a compound that confers upon the plant tissue resistance to an otherwise toxic compound. Genes of interest for use as a selectable, screenable, or scorable marker would include but are not limited to GUS, green fluorescent protein (GFP), luciferase (LUX), antibiotic or herbicide tolerance genes. Examples of antibiotic resistance genes include the penicillins, kanamycin (and neomycin, G418, bleomycin); methotrexate (and trimethoprim); chloramphenicol; kanamycin and tetracycline. Polynucleotide molecules encoding proteins involved in herbicide tolerance are known in the art, and include, but are not limited to a polynucleotide molecule encoding 5-enolpyruvylshikimate-3-phosphate synthase (EPSPS) described in U.S. Pat. No. 5,627,061 (Barry, et al.), U.S. Pat. No. 5,633,435 (Barry, et al.), and U.S. Pat. No. 6,040,497 (Spencer, et al.) and aroA described in U.S. Pat. No. 5,094,945 (Comai) for glyphosate tolerance; a polynucleotide molecule encoding bromoxynil nitrilase (Bxn) described in U.S. Pat. No. 4,810,648 (Duerrschnabel, et al.) for Bromoxynil tolerance; a polynucleotide molecule encoding phytoene desaturase (crtI) described in Misawa et al, (1993) Plant J. 4:833-840 and Misawa et al, (1994) Plant J. 6:481-489 for norflurazon tolerance; a polynucleotide molecule encoding acetohydroxyacid synthase (AHAS, aka ALS) described in Sathasiivan et al. (1990) Nucl. Acids Res. 18:2188-2193 for tolerance to sulfonylurea herbicides; and the bar gene described in DeBlock, et al. (1987) EMBO J. 6:2513-2519 for glufosinate and bialaphos tolerance.

The regeneration, development, and cultivation of plants from various transformed explants are well documented in the art. This regeneration and growth process typically includes the steps of selecting transformed cells and culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil. Cells that survive the exposure to the selective agent, or cells that have been scored positive in a screening assay, may be cultured in media that supports regeneration of plants. Developing plantlets are transferred to soil less plant growth mix, and hardened off, prior to transfer to a greenhouse or growth chamber for maturation.

The present invention can be used with any transformable cell or tissue. By transformable as used herein is meant a cell or tissue that is capable of further propagation to give rise to a plant. Those of skill in the art recognize that a number of plant cells or tissues are transformable in which after insertion of exogenous DNA and appropriate culture conditions the plant cells or tissues can form into a differentiated plant. Tissue suitable for these purposes can include but is not limited to immature embryos, scutellar tissue, suspension cell cultures, immature inflorescence, shoot meristem, nodal explants, callus tissue, hypocotyl tissue, cotyledons, roots, and leaves.

Any suitable plant culture medium can be used. Examples of suitable media would include but are not limited to MS-based media (Murashige and Skoog, Physiol. Plant, 15:473-497, 1962) or N6-based media (Chu et al., Scientia Sinica 18:659, 1975) supplemented with additional plant growth regulators including but not limited to auxins, cytokinins, ABA, and gibberellins. Those of skill in the art are familiar with the variety of tissue culture media, which when supplemented appropriately, support plant tissue growth and development and are suitable for plant transformation and regeneration. These tissue culture media can either be purchased as a commercial preparation, or custom prepared and modified. Those of skill in the art are aware that media and media supplements such as nutrients and growth regulators for use in transformation and regeneration and other culture conditions such as light intensity during incubation, pH, and incubation temperatures that can be optimized for the particular variety of interest.

One of ordinary skill will appreciate that, after an expression cassette is stably incorporated in transgenic plants and confirmed to be operable, it can be introduced into other plants by sexual crossing. Any of a number of standard breeding techniques can be used, depending upon the species to be crossed.

Identification of Plants with an Altered Oil Content Phenotype

We used an *Arabidopsis* activation tagging screen to identify the association between the gene we have identified and designated "HIO1004," (At4g10550, GI#30681486) encoding a subtilase family protein (GI# 18413353), and an altered oil content phenotype (specifically, a high oil phenotype). Briefly, and as further described in the Examples, a large number of *Arabidopsis* plants were mutated with the pSKI015 vector, which comprises a T-DNA from the Ti plasmid of *Agrobacterium tumifaciens*, a viral enhancer element, and a selectable marker gene (Weigel et al., 2000). When the T-DNA inserts into the genome of transformed plants, the enhancer element can cause up-regulation genes in the vicinity, generally within about 10 kilobase (kb) of the insertion. T1 plants were exposed to the selective agent in order to specifically recover transformed plants that expressed the selectable marker and therefore harbored T-DNA insertions. Samples of approximately 15-20 T2 seeds were collected from transformed T1 plants, and lipids were extracted from whole seeds. Gas chromatography (GC) analysis was performed to determine fatty acid content and composition of seed samples.

An *Arabidopsis* line that showed a high-oil phenotype was identified. The association of the HIO1004 gene with the high oil phenotype was discovered by analysis of the genomic DNA sequence flanking the T-DNA insertion in the identified line. Accordingly, HIO1004 genes and/or polypeptides may be employed in the development of genetically modified plants having a modified oil content phenotype ("a HIO1004 phenotype"). HIO1004 genes may be used in the generation of oilseed crops that provide improved oil yield from oilseed processing and in the generation of feed grain crops that provide increased energy for animal feeding. HIO1004 genes may further be used to increase the oil content of specialty oil crops, in order to augment yield of desired unusual fatty acids. Transgenic plants that have been genetically modified to express HIO1004 can be used in the production of oil, wherein the transgenic plants are grown, and oil is obtained from plant parts (e.g. seed) using standard methods.

HIO1004 Nucleic Acids and Polypeptides

*Arabidopsis* HIO1004 nucleic acid sequence is provided in SEQ ID NO:1 and in Genbank entry GI#30681486. The corresponding protein sequence is provided in SEQ ID NO:2 and in GI# 18413353. Nucleic acids and/or proteins that are orthologs or paralogs of *Arabidopsis* HIO1004, are described in Example 4 below.

As used herein, the term "HIO1004 polypeptide" refers to a full-length HIO1004 protein or a fragment, derivative (variant), or ortholog thereof that is "functionally active," meaning that the protein fragment, derivative, or ortholog exhibits one or more or the functional activities associated with the polypeptide of SEQ ID NO:2. In one preferred embodiment, a functionally active HIO1004 polypeptide causes an altered oil content phenotype when mis-expressed in a plant. In a further preferred embodiment, mis-expression of the HIO1004 polypeptide causes a high oil phenotype in a plant. In another embodiment, a functionally active HIO1004 polypeptide is capable of rescuing defective (including deficient) endogenous HIO1004 activity when expressed in a plant or in plant cells; the rescuing polypeptide may be from the same or from a different species as that with defective activity. In another embodiment, a functionally active fragment of a full length HIO1004 polypeptide (i.e., a native polypeptide having the sequence of SEQ ID NO:2 or a naturally occurring ortholog thereof) retains one of more of the biological properties associated with the full-length HIO1004 polypeptide, such as signaling activity, binding activity, catalytic activity, or cellular or extra-cellular localizing activity. A HIO1004 fragment preferably comprises a HIO1004 domain, such as a C- or N-terminal or catalytic domain, among others, and preferably comprises at least 10, preferably at least 20, more preferably at least 25, and most preferably at least 50 contiguous amino acids of a HIO1004 protein. Functional domains can be identified using the PFAM program (Bateman A et al., 1999 Nucleic Acids Res 27:260-262). A preferred HIO1004 fragment comprises of one or more subtilase domains.

Functionally active variants of full-length HIO1004 polypeptides or fragments thereof include polypeptides with amino acid insertions, deletions, or substitutions that retain one of more of the biological properties associated with the full-length HIO1004 polypeptide. In some cases, variants are generated that change the post-translational processing of a HIO1004 polypeptide. For instance, variants may have altered protein transport or protein localization characteristics or altered protein half-life compared to the native polypeptide.

As used herein, the term "HIO1004 nucleic acid" encompasses nucleic acids with the sequence provided in or complementary to the sequence provided in SEQ ID NO:1, as well as functionally active fragments, derivatives, or orthologs thereof. A HIO1004 nucleic acid of this invention may be DNA, derived from genomic DNA or cDNA, or RNA.

In one embodiment, a functionally active HIO1004 nucleic acid encodes or is complementary to a nucleic acid that encodes a functionally active HIO1004 polypeptide. Included within this definition is genomic DNA that serves as a template for a primary RNA transcript (i.e., an mRNA precursor) that requires processing, such as splicing, before encoding the functionally active HIO1004 polypeptide. A HIO1004 nucleic acid can include other non-coding sequences, which may or may not be transcribed; such sequences include 5' and 3'UTRs, polyadenylation signals and regulatory sequences that control gene expression, among others, as are known in the art. Some polypeptides require processing events, such as proteolytic cleavage, covalent modification, etc., in order to become fully active. Accordingly, functionally active nucleic acids may encode the mature or the pre-processed HIO1004 polypeptide, or an intermediate form. A HIO1004 polynucleotide can also include heterologous coding sequences, for example, sequences that encode a marker included to facilitate the purification of the fused polypeptide, or a transformation marker.

In another embodiment, a functionally active HIO1004 nucleic acid is capable of being used in the generation of loss-of-function HIO1004 phenotypes, for instance, via antisense suppression, co-suppression, etc.

In one preferred embodiment, a HIO1004 nucleic acid used in the methods of this invention comprises a nucleic acid sequence that encodes or is complementary to a sequence that encodes a HIO1004 polypeptide having at least 50%, 60%, 70%, 75%, 80%, 85%, 90%, 95% or more sequence identity to the polypeptide sequence presented in SEQ ID NO:2.

In another embodiment a HIO1004 polypeptide of the invention comprises a polypeptide sequence with at least 50% or 60% identity to the HIO1004 polypeptide sequence of SEQ ID NO:2, and may have at least 70%, 80%, 85%, 90% or 95% or more sequence identity to the HIO1004 polypeptide sequence of SEQ ID NO:2, such as one or more subtilisin or protein associated (PA) domains. In another embodiment, a HIO1004 polypeptide comprises a polypeptide sequence with at least 50%, 60%, 70%, 80%, 85%, 90% or 95% or more sequence identity to a functionally active fragment of the polypeptide presented in SEQ ID NO:2. In yet another embodiment, a HIO1004 polypeptide comprises a polypeptide sequence with at least 50%, 60%, 70%, 80%, or 90% identity to the polypeptide sequence of SEQ ID NO:2 over its entire length and comprises of one or more subtilisin or protein associated (PA) domains.

In another aspect, a HIO1004 polynucleotide sequence is at least 50% to 60% identical over its entire length to the HIO1004 nucleic acid sequence presented as SEQ ID NO:1, or nucleic acid sequences that are complementary to such a HIO1004 sequence, and may comprise at least 70%, 80%, 85%, 90% or 95% or more sequence identity to the HIO1004 sequence presented as SEQ ID NO:1 or a functionally active fragment thereof, or complementary sequences.

As used herein, "percent (%) sequence identity" with respect to a specified subject sequence, or a specified portion thereof, is defined as the percentage of nucleotides or amino acids in the candidate derivative sequence identical with the nucleotides or amino acids in the subject sequence (or specified portion thereof), after aligning the sequences and introducing gaps, if necessary to achieve the maximum percent sequence identity, as generated by the program WU-BLAST-2.0a19 (Altschul et al., J. Mol. Biol. (1997) 215:403-410) with search parameters set to default values. The HSP S and HSP S2 parameters are dynamic values and are established by the program itself depending upon the composition of the particular sequence and composition of the particular database against which the sequence of interest is being searched. A "% identity value" is determined by the number of matching identical nucleotides or amino acids divided by the sequence length for which the percent identity is being reported. "Percent (%) amino acid sequence similarity" is determined by doing the same calculation as for determining % amino acid sequence identity, but including conservative amino acid substitutions in addition to identical amino acids in the computation. A conservative amino acid substitution is one in which an amino acid is substituted for another amino acid having similar properties such that the folding or activity of the protein is not significantly affected. Aromatic amino acids that can be substituted for each other are phenylalanine, tryptophan, and tyrosine; interchangeable hydrophobic amino acids are leucine, isoleucine, methionine, and valine; interchangeable polar amino acids are glutamine and asparagine; interchangeable basic amino acids are arginine, lysine and histidine; interchangeable acidic amino acids are aspartic acid and glutamic acid; and interchangeable small amino acids are alanine, serine, threonine, cysteine and glycine.

Derivative nucleic acid molecules of the subject nucleic acid molecules include sequences that selectively hybridize to the nucleic acid sequence of SEQ ID NO:1. The stringency of hybridization can be controlled by temperature, ionic strength, pH, and the presence of denaturing agents such as formamide during hybridization and washing. Conditions routinely used are well known (see, e.g., Current Protocol in Molecular Biology, Vol. 1, Chap. 2.10, John Wiley & Sons, Publishers (1994); Sambrook et al., Molecular Cloning, Cold Spring Harbor (1989)). In some embodiments, a nucleic acid molecule of the invention is capable of hybridizing to a nucleic acid molecule containing the nucleotide sequence of SEQ ID NO:1 under stringent hybridization conditions that are: prehybridization of filters containing nucleic acid for 8 hours to overnight at 65° C. in a solution comprising 6× single strength citrate (SSC) (1×SSC is 0.15 M NaCl, 0.015 M Na citrate; pH 7.0), 5× Denhardt's solution, 0.05% sodium pyrophosphate and 100 µg/ml herring sperm DNA; hybridization for 18-20 hours at 65° C. in a solution containing 6×SSC, 1× Denhardt's solution, 100 µg/ml yeast tRNA and 0.05% sodium pyrophosphate; and washing of filters at 65° C. for 1 h in a solution containing 0.1×SSC and 0.1% SDS (sodium dodecyl sulfate). In other embodiments, moderately stringent hybridization conditions are used that are: pretreatment of filters containing nucleic acid for 6 h at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA; hybridization for 18-20 h at 40° C. in a solution containing 35% formamide, 5×SSC, 50 mM Tris-HCl (pH 7.5), 5 mM EDTA, 0.02% PVP, 0.02% Ficoll, 0.2% BSA, 100 µg/ml salmon sperm DNA, and 10% (wt/vol) dextran sulfate; followed by washing twice for 1 hour at 55° C. in a solution containing 2×SSC and 0.1% SDS. Alternatively, low stringency conditions can be used that comprise: incubation for 8 hours to overnight at 37° C. in a solution comprising 20% formamide, 5×SSC, 50 mM sodium phosphate (pH 7.6), 5× Denhardt's solution, 10% dextran sulfate, and 20 µg/ml denatured sheared salmon sperm DNA; hybridization in the same buffer for 18 to 20 hours; and washing of filters in 1×SSC at about 37° C. for 1 hour.

As a result of the degeneracy of the genetic code, a number of polynucleotide sequences encoding a HIO1004 polypeptide can be produced. For example, codons may be selected to increase the rate at which expression of the polypeptide occurs in a particular host species, in accordance with the optimum codon usage dictated by the particular host organism (see, e.g., Nakamura et al, 1999). Such sequence variants may be used in the methods of this invention.

The methods of the invention may use orthologs of the *Arabidopsis* HIO1004. Methods of identifying the orthologs in other plant species are known in the art. Normally, orthologs in different species retain the same function, due to presence of one or more protein motifs and/or 3-dimensional structures. In evolution, when a gene duplication event follows speciation, a single gene in one species, such as *Arabidopsis*, may correspond to multiple genes (paralogs) in another. As used herein, the term "orthologs" encompasses paralogs. When sequence data is available for a particular plant species, orthologs are generally identified by sequence homology analysis, such as BLAST analysis, usually using protein bait sequences. Sequences are assigned as a potential ortholog if the best hit sequence from the forward BLAST result retrieves the original query sequence in the reverse BLAST (Huynen M A and Bork P, Proc Natl Acad Sci (1998) 95:5849-5856; Huynen M A et al., Genome Research (2000) 10:1204-1210).

Programs for multiple sequence alignment, such as CLUSTAL (Thompson J D et al, 1994, Nucleic Acids Res 22:4673-4680) may be used to highlight conserved regions and/or residues of orthologous proteins and to generate phylogenetic trees. In a phylogenetic tree representing multiple homologous sequences from diverse species (e.g., retrieved through BLAST analysis), orthologous sequences from two species generally appear closest on the tree with respect to all other sequences from these two species. Structural threading or other analysis of protein folding (e.g., using software by ProCeryon, Biosciences, Salzburg, Austria) may also identify potential orthologs. Nucleic acid hybridization methods may also be used to find orthologous genes and are preferred when sequence data are not available. Degenerate PCR and screening of cDNA or genomic DNA libraries are common methods for finding related gene sequences and are well known in the art (see, e.g., Sambrook, 1989; Dieffenbach and Dveksler, 1995). For instance, methods for generating a cDNA library from the plant species of interest and probing the library with partially homologous gene probes are described in Sambrook et al. A highly conserved portion of the *Arabidopsis* HIO1004 coding sequence may be used as a probe. HIO1004 ortholog nucleic acids may hybridize to the nucleic acid of SEQ ID NO:1 under high, moderate, or low stringency conditions. After amplification or isolation of a segment of a putative ortholog, that segment may be cloned and sequenced by standard techniques and utilized as a probe to isolate a complete cDNA or genomic clone. Alternatively, it is possible to initiate an EST project to generate a database of sequence information for the plant species of interest. In another approach, antibodies that specifically bind known HIO1004 polypeptides are used for ortholog isolation (see, e.g., Harlow and Lane, 1988, 1999). Western blot analysis can determine that a HIO1004 ortholog (i.e., an orthologous protein) is present in a crude extract of a particular plant species. When reactivity is observed, the sequence encoding the candidate ortholog may be isolated by screening expression libraries representing the particular plant species. Expression libraries can be constructed in a variety of commercially available vectors, including lambda gt11, as described in Sambrook, et al., 1989. Once the candidate ortholog(s) are identified by any of these means, candidate orthologous sequence are used as bait (the "query") for the reverse BLAST against sequences from *Arabidopsis* or other species in which HIO1004 nucleic acid and/or polypeptide sequences have been identified.

HIO1004 nucleic acids and polypeptides may be obtained using any available method. For instance, techniques for isolating cDNA or genomic DNA sequences of interest by screening DNA libraries or by using polymerase chain reaction (PCR), as previously described, are well known in the art. Alternatively, nucleic acid sequence may be synthesized. Any known method, such as site directed mutagenesis (Kunkel T A et al., 1991), may be used to introduce desired changes into a cloned nucleic acid.

In general, the methods of the invention involve incorporating the desired form of the HIO1004 nucleic acid into a plant expression vector for transformation of in plant cells, and the HIO1004 polypeptide is expressed in the host plant.

An isolated HIO1004 nucleic acid molecule is other than in the form or setting in which it is found in nature and is identified and separated from least one contaminant nucleic acid molecule with which it is ordinarily associated in the natural source of the HIO1004 nucleic acid. However, an isolated HIO1004 nucleic acid molecule includes HIO1004 nucleic acid molecules contained in cells that ordinarily express HIO1004 where, for example, the nucleic acid molecule is in a chromosomal location different from that of natural cells.

Generation of Genetically Modified Plants with an Altered Oil Content Phenotype

HIO1004 nucleic acids and polypeptides may be used in the generation of genetically modified plants having a modified oil content phenotype. As used herein, a "modified oil content phenotype" may refer to modified oil content in any part of the plant; the modified oil content is often observed in seeds. In a preferred embodiment, altered expression of the HIO1004 gene in a plant is used to generate plants with a high oil phenotype.

The methods described herein are generally applicable to all plants. Although activation tagging and gene identification is carried out in *Arabidopsis*, the HIO1004 gene (or an ortholog, variant or fragment thereof) may be expressed in any type of plant. In a preferred embodiment, the invention is directed to oil-producing plants, which produce and store triacylglycerol in specific organs, primarily in seeds. Such species include soybean (*Glycine max*), rapeseed and canola (including *Brassica napus, B. campestris*), sunflower (*Helianthus annus*), cotton (*Gossypium hirsutum*), corn (*Zea mays*), cocoa (*Theobroma cacao*), safflower (*Carthamus tinctorius*), oil palm (*Elaeis guineensis*), coconut palm (*Cocos nucifera*), flax (*Linum usitatissimum*), castor (*Ricinus communis*) and peanut (*Arachis hypogaea*). The invention may also be directed to fruit- and vegetable-bearing plants, grain-producing plants, nut-producing plants, rapid cycling *Brassica* species, alfalfa (*Medicago sativa*), tobacco (*Nicotiana*), turfgrass (Poaceae family), other forage crops, and wild species that may be a source of unique fatty acids.

The skilled artisan will recognize that a wide variety of transformation techniques exist in the art, and new techniques are continually becoming available. Any technique that is suitable for the target host plant can be employed within the scope of the present invention. For example, the constructs can be introduced in a variety of forms including, but not limited to as a strand of DNA, in a plasmid, or in an artificial chromosome. The introduction of the constructs into the target plant cells can be accomplished by a variety of techniques, including, but not limited to *Agrobacterium*-mediated transformation, electroporation, microinjection, microprojectile bombardment calcium-phosphate-DNA co-precipitation or liposome-mediated transformation of a heterologous nucleic acid. The transformation of the plant is preferably permanent, i.e. by integration of the introduced expression constructs into the host plant genome, so that the introduced constructs are passed onto successive plant generations. Depending upon the intended use, a heterologous nucleic acid construct comprising an HIO1004 polynucleotide may encode the entire protein or a biologically active portion thereof.

In one embodiment, binary Ti-based vector systems may be used to transfer polynucleotides. Standard *Agrobacterium* binary vectors are known to those of skill in the art, and many are commercially available (e.g., pBI121 Clontech Laboratories, Palo Alto, Calif.). A construct or vector may include a plant promoter to express the nucleic acid molecule of choice. In a preferred embodiment, the promoter is a plant promoter.

The optimal procedure for transformation of plants with *Agrobacterium* vectors will vary with the type of plant being transformed. Exemplary methods for *Agrobacterium*-mediated transformation include transformation of explants of hypocotyl, shoot tip, stem or leaf tissue, derived from sterile seedlings and/or plantlets. Such transformed plants may be reproduced sexually, or by cell or tissue culture. *Agrobacterium* transformation has been previously described for a large number of different types of plants and methods for such transformation may be found in the scientific literature. Of particular relevance are methods to transform commercially important crops, such as rapeseed (De Block et al., 1989), sunflower (Everett et al., 1987), and soybean (Christou et al., 1989; Kline et al., 1987).

Expression (including transcription and translation) of HIO1004 may be regulated with respect to the level of expression, the tissue type(s) where expression takes place and/or developmental stage of expression. A number of heterologous regulatory sequences (e.g., promoters and enhancers) are available for controlling the expression of a HIO1004 nucleic acid. These include constitutive, inducible and regulatable promoters, as well as promoters and enhancers that control expression in a tissue- or temporal-specific manner. Exemplary constitutive promoters include the raspberry E4 promoter (U.S. Pat. Nos. 5,783,393 and 5,783,394), the nopaline synthase (NOS) promoter (Ebert et al., *Proc. Natl. Acad. Sci.* (U.S.A.) 84:5745-5749, 1987), the octopine synthase (OCS) promoter (which is carried on tumor-inducing plasmids of *Agrobacterium tumefaciens*), the caulimovirus promoters such as the cauliflower mosaic virus (CaMV) 19S promoter (Lawton et al., *Plant Mol. Biol.* 9:315-324, 1987) and the CaMV 35S promoter (Odell et al., *Nature* 313:810-812, 1985 and Jones JD et al, 1992), the melon actin promoter (published PCT application WO0056863), the figwort mosaic virus 35S-promoter (U.S. Pat. No. 5,378,619), the light-inducible promoter from the small subunit of ribulose-1,5-bis-phosphate carboxylase (ssRUBISCO), the Adh promoter (Walker et al., *Proc. Natl. Acad. Sci.* (U.S.A.) 84:6624-6628, 1987), the sucrose synthase promoter (Yang et al., *Proc. Natl. Acad. Sci.* (U.S.A.) 87:4144-4148, 1990), the R gene complex promoter (Chandler et al., *The Plant Cell* 1:1175-1183, 1989), the chlorophyll a/b binding protein gene promoter the CsVMV promoter (Verdaguer B et al., 1998); these promoters have been used to create DNA constructs that have been expressed in plants, e.g., PCT publication WO 84/02913. Exemplary tissue-specific promoters include the tomato E4 and E8 promoters (U.S. Pat. No. 5,859,330) and the tomato 2AII gene promoter (Van Haaren MJJ et al., 1993).

In one preferred embodiment, HIO1004 expression is under control of regulatory sequences from genes whose expression is associated with early seed and/or embryo development. Indeed, in a preferred embodiment, the promoter used is a seed-enhanced promoter. Examples of such promoters include the 5' regulatory regions from such genes as napin (Kridl et al., *Seed Sci. Res.* 1:209:219, 1991), globulin (Belanger and Kriz, *Genet.*, 129: 863-872, 1991, GenBank Accession No. L22295), gamma zein Z 27 (Lopes et al., *Mol Gen Genet.*, 247:603-613, 1995), L3 oleosin promoter (U.S. Pat. No. 6,433,252), phaseolin (Bustos et al., *Plant Cell*, 1(9):839-853, 1989), arcelin5 (US 2003/0046727), a soybean 7S promoter, a 7Sα promoter (US 2003/0093828), the soybean 7Sα' beta conglycinin promoter, a 7S α' promoter (Beachy et al., *EMBO J.*, 4:3047, 1985; Schuler et al., *Nucleic Acid Res.*, 10(24):8225-8244, 1982), soybean trypsin inhibitor (Riggs et al., *Plant Cell* 1(6):609-621, 1989), ACP (Baerson et al., *Plant Mol. Biol.*, 22(2):255-267, 1993), stearoyl-ACP desaturase (Slocombe et al., *Plant Physiol.* 104(4):167-

176, 1994), soybean a' subunit of β-conglycinin (Chen et al., *Proc. Natl. Acad. Sci.* 83:8560-8564, 1986), *Vicia faba* USP (P-Vf.Usp, SEQ ID NO: 1, 2, and 3 in (US 2003/229918) and *Zea mays* L3 oleosin promoter (Hong et al., *Plant Mol. Biol.,* 34(3):549-555, 1997). Also included are the zeins, which are a group of storage proteins found in corn endosperm. Genomic clones for zein genes have been isolated (Pedersen et al., *Cell* 29:1015-1026, 1982; and Russell et al., *Transgenic Res.* 6(2):157-168) and the promoters from these clones, including the 15 kD, 16 kD, 19 kD, 22 kD, 27 kD and genes, could also be used. Other promoters known to function, for example, in corn include the promoters for the following genes: waxy, Brittle, Shrunken 2, Branching enzymes I and II, starch synthases, debranching enzymes, oleosins, glutelins and sucrose synthases. Legume genes whose promoters are associated with early seed and embryo development include *V. faba* legumin (Baumlein et al., 1991, Mol Gen Genet 225: 121-8; Baumlein et al., 1992, Plant J 2:233-9), *V. faba* usp (Fiedler et al., 1993, Plant Mol Biol 22:669-79), pea convicilin (Bown et al., 1988, Biochem J 251:717-26), pea lectin (dePater et al., 1993, Plant Cell 5:877-86), *P. vulgaris* beta phaseolin (Bustos et al., 1991, EMBO J 10:1469-79), *P. vulgaris* DLEC2 and PHS [beta] (Bobb et al, 1997, Nucleic Acids Res 25:641-7), and soybean beta-Conglycinin, 7S storage protein (Chamberland et al., 1992, Plant Mol Biol 19:937-49).

Cereal genes whose promoters are associated with early seed and embryo development include rice glutelin ("GluA-3," Yoshihara and Takaiwa, 1996, Plant Cell Physiol 37:107-11; "GluB-1," Takaiwa et al., 1996, Plant Mol Biol 30:1207-21; Washida et al., 1999, Plant Mol Biol 40:1-12; "Gt3," Leisy et al., 1990, Plant Mol Biol 14:41-50), rice prolamin (Zhou & Fan, 1993, Transgenic Res 2:141-6), wheat prolamin (Hammond-Kosack et al., 1993, EMBO J 12:545-54), maize zein (Z4, Matzke et al., 1990, Plant Mol Biol 14:323-32), and barley B-hordeins (Entwistle et al., 1991, Plant Mol Biol 17:1217-31).

Other genes whose promoters are associated with early seed and embryo development include oil palm GLO7A (7S globulin, Morcillo et al., 2001, Physiol Plant 112:233-243), *Brassica napus* napin, 2S storage protein, and napA gene (Josefsson et al., 1987, J Biol Chem 262:12196-201; Stalberg et al., 1993, Plant Mol Biol 1993 23:671-83; Ellerstrom et al., 1996, Plant Mol Biol 32:1019-27), *Brassica napus* oleosin (Keddie et al., 1994, Plant Mol Biol 24:327-40), *Arabidopsis oleosin* (Plant et al., 1994, Plant Mol Biol 25:193-205), *Arabidopsis* FAE1 (Rossak et al., 2001, Plant Mol Biol 46:717-25), *Canavalia gladiata* conA (Yamamoto et al., 1995, Plant Mol Biol 27:729-41), and *Catharanthus roseus* strictosidine synthase (Str, Ouwerkerk and Memelink, 1999, Mol Gen Genet 261:635-43). In another preferred embodiment, regulatory sequences from genes expressed during oil biosynthesis are used (see, e.g., U.S. Pat. No. 5,952,544). Alternative promoters are from plant storage protein genes (Bevan et al, 1993, Philos Trans R Soc Lond B Biol Sci 342:209-15). Additional promoters that may be utilized are described, for example, in U.S. Pat. Nos. 5,378,619; 5,391,725; 5,428,147; 5,447,858; 5,608,144; 5,608,144; 5,614,399; 5,633,441; 5,633,435; and 4,633,436.

In yet another aspect, in some cases it may be desirable to inhibit the expression of endogenous HIO1004 in a host cell. Exemplary methods for practicing this aspect of the invention include, but are not limited to antisense suppression (Smith, et al., 1988; van der Krol et al., 1988); co-suppression (Napoli, et al., 1990); ribozymes (PCT Publication WO 97/10328); and combinations of sense and antisense (Waterhouse et al., 1998). Methods for the suppression of endogenous sequences in a host cell typically employ the transcription or transcription and translation of at least a portion of the sequence to be suppressed. Such sequences may be homologous to coding as well as non-coding regions of the endogenous sequence. Antisense inhibition may use the entire cDNA sequence. (Sheehy et al., 1988), a partial cDNA sequence including fragments of 5' coding sequence, (Cannon et al., 1990), or 3' non-coding sequences (Ch'ng et al., 1989). Cosuppression techniques may use the entire cDNA sequence (Napoli et al., 1990; van der Krol et al., 1990), or a partial cDNA sequence (Smith et al., 1990).

Standard molecular and genetic tests may be performed to further analyze the association between a gene and an observed phenotype. Exemplary techniques are described below.

1. DNA/RNA Analysis

The stage- and tissue-specific gene expression patterns in mutant versus wild-type lines may be determined, for instance, by in situ hybridization. Analysis of the methylation status of the gene, especially flanking regulatory regions, may be performed. Other suitable techniques include overexpression, ectopic expression, expression in other plant species and gene knock-out (reverse genetics, targeted knock-out, viral induced gene silencing [VIGS, see Baulcombe D, 1999]).

In a preferred application expression profiling, generally by microarray analysis, is used to simultaneously measure differences or induced changes in the expression of many different genes. Techniques for microarray analysis are well known in the art (Schena M et al., Science (1995) 270:467-470; Baldwin D et al., 1999; Dangond F, Physiol Genomics (2000) 2:53-58; van Hal N L et al., J Biotechnol (2000) 78:271-280; Richmond T and Somerville S, Curr Opin Plant Biol (2000) 3:108-116). Expression profiling of individual tagged lines may be performed. Such analysis can identify other genes that are coordinately regulated as a consequence of the overexpression of the gene of interest, which may help to place an unknown gene in a particular pathway.

2. Gene Product Analysis

Analysis of gene products may include recombinant protein expression, antisera production, immunolocalization, biochemical assays for catalytic or other activity, analysis of phosphorylation status, and analysis of interaction with other proteins via yeast two-hybrid assays.

3. Pathway Analysis

Pathway analysis may include placing a gene or gene product within a particular biochemical, metabolic or signaling pathway based on its mis-expression phenotype or by sequence homology with related genes. Alternatively, analysis may comprise genetic crosses with wild-type lines and other mutant lines (creating double mutants) to order the gene in a pathway, or determining the effect of a mutation on expression of downstream "reporter" genes in a pathway.

Generation of Mutated Plants with an Altered Oil Content Phenotype

The invention further provides a method of identifying plants that have mutations in endogenous HIO1004 that confer altered oil content, and generating altered oil content progeny of these plants that are not genetically modified. In one method, called "TILLING" (for targeting induced local lesions in genomes), mutations are induced in the seed of a plant of interest, for example, using EMS treatment. The resulting plants are grown and fertilized, and the progeny are used to prepare DNA samples. HIO1004-specific PCR is used to identify whether a mutated plant has a HIO1004 mutation. Plants having HIO1004 mutations may then be tested for altered oil content, or alternatively, plants may be tested for altered oil content, and then HIO1004-specific PCR is used to determine whether a plant having altered oil content has a mutated HIO1004 gene. TILLING can identify mutations that may alter the expression of specific genes or the activity of proteins encoded by these genes (see Colbert et al (2001) Plant Physiol 126:480-484; McCallum et al (2000) Nature Biotechnology 18:455-457).

In another method, a candidate gene/Quantitative Trait Locus (QTLs) approach can be used in a marker-assisted breeding program to identify alleles of or mutations in the HIO1004 gene or orthologs of HIO1004 that may confer altered oil content (see Bert et al., Theor Appl Genet. 2003 June; 107(1):181-9; and Lionneton et al, Genome. 2002 December; 45(6):1203-15). Thus, in a further aspect of the invention, a HIO1004 nucleic acid is used to identify whether a plant having altered oil content has a mutation in endogenous HIO1004 or has a particular allele that causes altered oil content.

While the invention has been described with reference to specific methods and embodiments, it will be appreciated that various modifications and changes may be made without departing from the invention. All publications cited herein are expressly incorporated herein by reference for the purpose of describing and disclosing compositions and methodologies that might be used in connection with the invention. All cited patents, patent applications, and sequence information in referenced websites and public databases are also incorporated by reference.

EXAMPLES

Example 1

Generation of Plants with a HIO1004 Phenotype by Transformation with an Activation Tagging Construct Mutants were generated using the activation tagging "ACTTAG" vector, pSKI015 (GI#6537289; Weigel D et al., 2000). Standard methods were used for the generation of *Arabidopsis* transgenic plants, and were essentially as described in published application PCT WO0183697. Briefly, T0 *Arabidopsis* (Col-0) plants were transformed with *Agrobacterium* carrying the pSKI015 vector, which comprises T-DNA derived from the *Agrobacterium* Ti plasmid, an herbicide resistance selectable marker gene, and the 4× CaMV 35S enhancer element. Transgenic plants were selected at the T1 generation based on herbicide resistance.

T3 seed was analyzed by Near Infrared Spectroscopy (NIR) at the time of harvest. NIR infrared spectra were captured using a Bruker 22 N/F. Bruker Software was used to estimate total seed oil and total seed protein content using data from NIR analysis and reference methods according to the manufacturers instructions. Oil contents predicted by our calibration (ren oil 1473 1d+sline.q2, Predicts Hexane Extracted Oil), which followed the general method of AOCS Procedure AM1-92, Official Methods and Recommended Practices of the American Oil Chemists Society, 5th Ed., AOCS, Champaign, Ill., were compared for 38,090 individual ACTTAG lines. Subsequent to seed compositional analysis, the position of the ACTTAG element in the genome of each line was determined by inverse PCR and sequencing. 38,090 lines with recovered flanking sequences were considered in this analysis.

Since the 38,090 lines were planted and grown over a 12-month period, the seed oil content values were normalized to minimize the effect of environmental differences which may alter seed oil content. The average seed oil content and its standard deviation, for each day lines were planted, were calculated. The seed oil content was expressed as a "relative standard deviation distance" (SD distance) which was calculated by subtracting the average seed oil content for the planting day from seed oil content for each line and dividing the difference by the standard deviation for that day. This normalization allows comparison of seed oil content in seed from plants grown throughout the year.

Genes that cause a high seed oil phenotype when over-expressed were identified by evaluating all of the genes affected by ACTTAG elements in the 38,090 lines. This was accomplished by the following procedure; first, the genes likely to be activated by the ACTTAG element in each line were identified and the seed oil content of the line was assigned to these genes; second, the seed oil content when a particular gene is over-expressed was determined by averaging the individual seed oil values for each gene. Since 38,090 lines were evaluated and each element affects an average of 2.5 genes, each gene will have an average of 4 seed oil values. The genes with the highest average SD distance were determined to be those that cause a high seed oil phenotype when over-expressed.

The oil content and "relative standard deviation distance" of plants over-expressing At4g10550, HIO1004 is shown in the following Table 1.

TABLE 1

| Tair | relative standard deviation distance | plant count | Description | Line ID | Planting date | n (# of ACTTAG lines planted for the date with NIR measurement) | Seed Oil content (%) | Average oil content of the planting date (%) | Standard deviation of the oil content for the planting date |
|---|---|---|---|---|---|---|---|---|---|
| At4g10550 | 2.851811 | 1 | subtilisin-like serine protease | W000198284 | Sept. 25, 2002 | 1030 | 36.176 | 29.774 | 2.245 |

Example 2

Characterization of the T-DNA Insertion in Plants Exhibiting the Altered Oil Content Phenotype.

We performed standard molecular analyses, essentially as described in patent application PCT WO0183697, to determine the site of the T-DNA insertion associated with the altered oil content phenotype. Briefly, genomic DNA was extracted from plants exhibiting the altered oil content phenotype. PCR, using primers specific to the pSKI015 vector, confirmed the presence of the 35S enhancer in plants from the HIO1004 oil line, and Southern blot analysis verified the genomic integration of the ACTTAG T-DNA and showed the presence of the T-DNA insertions in each of the transgenic lines.

Inverse PCR was used to recover genomic DNA flanking the T-DNA insertion, which was then subjected to sequence analysis using a basic BLASTN search and/or a search of the *Arabidopsis* Information Resource (TAIR) database (available at the arabidopsis.org website).

Example 3

Recapitulation of HIO1004 Phenotype

To test whether over-expression of At4g10550 causes a high seed oil phenotype, oil content in seeds from transgenic plants over-expressing this gene was compared with oil content in seeds from non-transgenic control plants. To do this, At4g10550 was cloned into a plant transformation vector behind the seed specific CsVMV promoter and transformed into *Arabidopsis* plants using the floral dip method. The plant transformation vector contains the nptII gene driven by the RE4 promoter, to provide resistance to kanamyacin, and serve as a selectable marker. Seed from the transformed plants were plated on agar medium containing kanamycin. After 7 days, transgenic plants were identified as healthy green plants and transplanted to soil. Non-transgenic control plants were germinated on agar medium, allowed to grow for 7 days and then transplanted to soil. Twenty-two transgenic seedlings and 10 non-transgenic control plants were transplanted to random positions in the same 32 cell flat. The plants were grown to maturity, allowed to self-fertilize and set seed. Seed was harvested from each plant and its oil content estimated by Near Infrared (NIR) Spectroscopy using methods previously described. The percent oil in the seed harvested from each plant as determined by NIR spectroscopy is presented in Table 3. The Relative Oil value is determined by dividing the predicted oil value by the average oil value in control seed (i.e. seed from plants without the trangene).

The effect of over-expression of At4g10550 on seed oil has been tested in two experiments. In both experiments, the plants over-expressing At4g10550 had higher seed oil content than the control plants grown in the same flat. Across the experiments, the average seed oil content of plants over-expressing At4g10550 was 5.0% greater than the untransformed controls. The seed oil content in plants over-expressing At4g10550 was significantly greater than non-transgenic control plants (two-way ANOVA; P=0.0134).

TABLE 2

| Experiment | Plant | Transgene | Percent Oil | Relative Oil |
|---|---|---|---|---|
| 1 | DX07124001 | CsVMV:At4g10550 | 35.45 | 112.41 |
| 1 | DX07124002 | CsVMV:At4g10550 | 32.84 | 104.15 |
| 1 | DX07124003 | CsVMV:At4g10550 | 35.8 | 113.53 |
| 1 | DX07124004 | CsVMV:At4g10550 | 34.18 | 108.4 |
| 1 | DX07124005 | CsVMV:At4g10550 | 36.75 | 116.55 |
| 1 | DX07124006 | CsVMV:At4g10550 | 32.46 | 102.96 |
| 1 | DX07124007 | CsVMV:At4g10550 | 32.69 | 103.68 |
| 1 | DX07124008 | CsVMV:At4g10550 | 35.91 | 113.89 |
| 1 | DX07124009 | CsVMV:At4g10550 | 35.51 | 112.62 |
| 1 | DX07124010 | CsVMV:At4g10550 | 30.63 | 97.13 |
| 1 | DX07124011 | CsVMV:At4g10550 | 27.88 | 88.41 |
| 1 | DX07124012 | CsVMV:At4g10550 | 32.2 | 102.1 |
| 1 | DX07124013 | CsVMV:At4g10550 | 33.98 | 107.76 |
| 1 | DX07124014 | CsVMV:At4g10550 | 35.41 | 112.31 |
| 1 | DX07124015 | CsVMV:At4g10550 | 33.04 | 104.8 |
| 1 | DX07124017 | CsVMV:At4g10550 | 30.85 | 97.83 |
| 1 | DX07124018 | CsVMV:At4g10550 | 26.81 | 85.03 |
| 1 | DX07124019 | CsVMV:At4g10550 | 33.2 | 105.29 |

TABLE 2-continued

| Experiment | Plant | Transgene | Percent Oil | Relative Oil |
|---|---|---|---|---|
| 1 | DX07124020 | CsVMV:At4g10550 | 29.61 | 93.92 |
| 1 | DX07124022 | CsVMV:At4g10550 | 35.58 | 112.84 |
| 1 | DX07142001 | None | 31.45 | 99.73 |
| 1 | DX07142002 | None | 32.26 | 102.32 |
| 1 | DX07142003 | None | 29.89 | 94.8 |
| 1 | DX07142004 | None | 31.67 | 100.44 |
| 1 | DX07142005 | None | 32.41 | 102.77 |
| 1 | DX07142006 | None | 29.82 | 94.56 |
| 1 | DX07142007 | None | 30.37 | 96.3 |
| 1 | DX07142008 | None | 30.69 | 97.34 |
| 1 | DX07142009 | None | 33.26 | 105.5 |
| 1 | DX07142010 | None | 33.5 | 106.25 |
| 2 | DX07169001 | CsVMV:At4g10550 | 32.31 | 112.36 |
| 2 | DX07169003 | CsVMV:At4g10550 | 32.73 | 113.8 |
| 2 | DX07169004 | CsVMV:At4g10550 | 27.65 | 96.15 |
| 2 | DX07169005 | CsVMV:At4g10550 | 31.12 | 108.23 |
| 2 | DX07169006 | CsVMV:At4g10550 | 30.32 | 105.43 |
| 2 | DX07169007 | CsVMV:At4g10550 | 26.81 | 93.21 |
| 2 | DX07169008 | CsVMV:At4g10550 | 30.22 | 105.07 |
| 2 | DX07169009 | CsVMV:At4g10550 | 29.84 | 103.77 |
| 2 | DX07169010 | CsVMV:At4g10550 | 30.51 | 106.08 |
| 2 | DX07169011 | CsVMV:At4g10550 | 31.17 | 108.38 |
| 2 | DX07169013 | CsVMV:At4g10550 | 33.02 | 114.81 |
| 2 | DX07169014 | CsVMV:At4g10550 | 28.9 | 100.49 |
| 2 | DX07169015 | CsVMV:At4g10550 | 29.19 | 101.48 |
| 2 | DX07187001 | None | 31.04 | 107.93 |
| 2 | DX07187002 | None | 29.29 | 101.83 |
| 2 | DX07187003 | None | 28.4 | 98.76 |
| 2 | DX07187004 | None | 30.6 | 106.4 |
| 2 | DX07187005 | None | 27 | 93.87 |
| 2 | DX07187006 | None | 28.22 | 98.14 |
| 2 | DX07187007 | None | 27.93 | 97.1 |
| 2 | DX07187008 | None | 28.7 | 99.79 |
| 2 | DX07187009 | None | 28.38 | 98.69 |
| 2 | DX07187010 | None | 28.04 | 97.5 |

Example 4

Analysis of *Arabidopsis* HIO1004 Sequence

Sequence analyses were performed with BLAST (Altschul et al., 1990, J. Mol. Biol. 215:402-410), PFAM (Bateman et al., 1999, Nucleic Acids Res 27:260-262), PSORT (Nakai K, and Horton P, 1999, Trends Biochem Sci 24:34-6), and/or CLUSTAL (Thompson J D et al., 1994, Nucleic Acids Res 22:4673-4680).

TBLASTN Against ESTs:

The candidate gene At4g10550 is supported by the full-length cDNA gi:22136593. There are many ESTs from diverse plant species showing similarity to At4g10550. Where possible, ESTs contigs of each species were made. The top hit for each of the following species are listed below and included in the orthologue Table 2: *Triticum aestivum, Glycine max, Mentha×piperita, Populus tremula, Oryza sativa, Lycopersicon esculentum, Solanum tuberosum,* and *Beta vulgaris*.

1. Sugar Beet ESTs with the Following GenBank IDS:
gi|10711340

2. Potato ESTs with the Following GenBank IDS:
gi|10446020
gi|10446024
gi|13612262
gi|13613712
gi|14264360
gi|14267180
gi|15185273

3. Tomato ESTs with the Following GenBank IDS:
gi|6536422
gi|6536423
gi|6536424
gi|6536425
gi|1771159
gi|1771159
gi|1771160

4. Rice ESTs with the Following GenBank IDS:
gi|9453866

5. Poplar ESTs with the Following GenBank IDS:
gi|3852817
gi|3854402
gi|18012433
gi|23988298
gi|23991758
gi|24099801
gi|27419447
gi|27419568
gi|27419599
gi|27419823
gi|27420015
gi|27420028
gi|27420265
gi|33183186
gi|33183327
gi|33184237
gi|33185612

6. Soybean ESTs with the Following GenBank IDS:
gi|14150445
gi|13478114
gi|26057369

7. Corn ESTs with the Following GenBank IDS:
gi|6827742
gi|21208160
gi|12045659
gi|18164698
gi|29130115

8. Cotton ESTs with the Following GenBank IDS:
gi|5049444
gi|5049221
gi|5048791
gi|5046192
gi|5046014
gi|5045524

9. Wheat ESTs with the Following GenBank IDS:
gi|14313023
gi|14313024
gi|14313383
gi|14313807
gi|14314440
gi|14314549
gi|14316759
gi|14316760
gi|14317648
gi|15315409
gi|15772265
gi|19956142
gi|20048856
gi|20086046
gi|25157476
gi|25218457
gi|25238573
gi|32559310

BLASTP Against Amino Acids:

The protein At4g10550 has homology to subtilisin-like serine protease other organisms. Detailed phylogenetic analysis of proteases from *Arabidopsis* showed that At4g10550 is a member of the S8-1 serine protease of which there are 39 members (Beers, E., et al., Phytochemistry 2004, 65:43-58). It was shown that At4g10550 is closely related to At4g10540, At4g10510, At1g32940, At1g32950 and At1g32960. These proteins are likely to perform similar functions in planta. The top 10 BLAST results for At4g10550 are listed below and are included in the Orthologue Table 2 below.

1. At4g10550 itself from *Arabidopsis thaliana*
gi|18413353|ref|NP_567362.1| subtilase family protein [*Arabidopsis thaliana*]
gi|22136594|gb|AAM91616.1| putative subtilisin serine protease [*Arabidopsis thaliana*]
Length=778
Score=4003, P=0.000000e+00
Identities=98%, Positives=98%

The following sequences are other redundant entries of At4g10550 according to the *Arabidopsis* information resource website. However, they differ from the sequences listed above by a few nucleotides. This is likely to be the result of sequencing errors or of single nucleotide polymorphisms with little or no effect on activity.
>gi|7435680|pir||T04190 subtilisin-like proteinase homolog T4F9.10—*Arabidopsis thaliana*
>gi|4539433|emb|CAB40021.1| subtilisin-like protease-like protein [*Arabidopsis thaliana*]
>gi|7267752|emb|CAB78178.1| subtilisin-like protease-like protein [*Arabidopsis thaliana*]
Length=803
Score=3243 (1146.7 bits), Expect=0., Sum P(2)=0.
Identities=619/637 (97%), Positives=622/637 (97%)

The following sequence is another redundant entry of At4g10550 because it blasts to the At4g10550 locus in the *Arabidopsis* genome. However, it differs from the sequences listed above by a few nucleotides. This is likely to be the result of sequencing errors or of single nucleotide polymorphisms with little or no effect on activity
gi|4115920|gb|AAD03431.1| similar to the subtilase family of serine proteases(Pfam: PF00082, score; 45.8, E=1.1e−11, n=2) [*Arabidopsis thaliana*]
Length=751
Score=1902, P=0.000000e+00
Identities=95%, Positives=95%

2. At4g10540 from *Arabidopsis thaliana*
gi|18413351|ref|NP_567361.1| subtilase family protein [*Arabidopsis thaliana*]
gi|74356781|pir||T04189 subtilisin-like proteinase homolog F7L13.120—*Arabidopsis thaliana*
gi|4539414|emb|CAB40047.1|putative subtilisin-like protease [*Arabidopsis thaliana*]
gi|7267751|emb|CAB78177.1| putative subtilisin-like protease [*Arabidopsis thaliana*]
Length=775
Score=3342, P=0.000000e+00
Identities=81%, Positives=88%

The following sequence is another redundant entry of At4g10540 because it blasts to the At4g10540 locus in the *Arabidopsis* genome. However, it differs from the sequences listed above by a few nucleotides. This is likely to be the result of sequencing errors or of single nucleotide polymorphisms with little or no effect on activity >gi|4115919|gb|AAD03430.1| similar to the subtilase family of serine proteases (Pfam: PF00082, score; 47.5, E=3.8e-12, n=2) [*Arabidopsis thaliana*]
Length=685
Score=1535 (545.4 bits), Expect=9.7e-295, Sum P(3)=9.7e-295
Identities=291/380 (76%), Positives=324/380 (85%)

3. At4g10510 from *Arabidopsis thaliana*
gi|18413345|ref|NP_567358.1| subtilase family protein [*Arabidopsis thaliana*]
gi|7435679|pir||T04186 subtilisin-like proteinase homolog F7L13.90—*Arabidopsis thaliana*
gi|4539411|emb|CAB40044.1| putative subtilisin-like protease [*Arabidopsis thaliana*]
gi|7267748|emb|CAB78174.1| putative subtilisin-like protease[*Arabidopsis thaliana*]
Length=765
Score=3244, P=0.000000e+00
Identities=82%, Positives=89%

The following sequence is another redundant entry of At4g10510. However, it differs from the sequence listed above by a few nucleotides. This is likely to be the result of sequencing errors or of single nucleotide polymorphisms with little or no effect on activity.
gi|4115927|gb|AAD03438.1| similar to the subtilase family of serine proteases (Pfam: PF00082, Score=49.7, E=9.2e-13, n=3) [*Arabidopsis thaliana*]
Length=774
Score=3219, P=0.000000e+00
Identities=81%, Positives=88%

4. At1g32950 from *Arabidopsis thaliana*
gi|30692782|ref|NP_564413.2| subtilase family protein [*Arabidopsis thaliana*]
Length=773
Score=3123, P=0.000000e+00
Identities=76%, Positives=85%

The following sequence is another redundant entry of At1g32950. However, it differs from the sequence listed above by a few nucleotides. This is likely to be the result of sequencing errors or of single nucleotide polymorphisms with little or no effect on activity.
>gi|25289836|pir||B86454 hypothetical protein F9L11.12—*Arabidopsis thaliana*
>gi|6910572|gb|AAF31277.1| Second of four adjacent putative subtilase family>[*Arabidopsis thaliana*]
Length=763
Score=3050 (1078.7 bits), Expect=2.7e-317, P=2.7e-317
Identities=588/779 (75%), Positives=659/779 (84%)

5. At1g32940 from *Arabidopsis thaliana*
gi|18398655|ref|NP_564412.1| subtilase family protein [*Arabidopsis thaliana*]
gi|25289835|pir||A86454 hypothetical protein F9L11.11—*Arabidopsis thaliana*
gi|6910573|gb|AAF31278.1| First of four adjacent putative subtilase family [*Arabidopsis thaliana*]
gi|18377745|gb|AAL67022.1| putative subtilisin serine protease [*Arabidopsis thaliana*]
gi|29824343|gb|AAP04132.1| putative subtilisin serine protease [*Arabidopsis thaliana*]
Length=774
Score=3100, P=0.000000e+00
Identities=75%, Positives=85%

6. At1g32960 from *Arabidopsis thaliana*
gi|30692785|ref|NP_564414.2| subtilase family protein [*Arabidopsis thaliana*]
gi|25289832|pir||C86454 hypothetical protein F9L11.13—*Arabidopsis thaliana*
gi|6910571|gb|AAF31276.1| Third of four adjacent putative subtilase family [*Arabidopsis thaliana*]
gi|20466548|gb|AAM20591.1| subtilase, putative [*Arabidopsis thaliana*]
gi|34098815|gb|AAQ56790.1| At1g32960 [*Arabidopsis thaliana*]
Length=777
Score=3053, P=2.700000e-317
Identities=74%, Positives=84%

7. At1g32970 from *Arabidopsis thaliana*
gi|15223351|ref|NP_174573.1| subtilase family protein [*Arabidopsis thaliana*]
gi|25289833|pir||D86454 F9L11.14 F9L11.14—*Arabidopsis thaliana*
gi|6910574|gb|AAF31279.1| Fourth of four adjacent putative subtilase family [*Arabidopsis thaliana*]
Length=734
Score=2021, P=3.600000e-237
Identities=67%, Positives=80%

8. At4g21650 from *Arabidopsis thaliana*
gi|30685518|ref|NP_567633.2| subtilase family protein [*Arabidopsis thaliana*]
gi|27311663|gb|AAO00797.1| subtilisin proteinase-like [*Arabidopsis thaliana*]
Length=766
Score=2187, P=9.600000e-226
Identities=56%, Positives=71%

9. At4g21640 from *Arabidopsis thaliana*
gi|42567017|ref|NP_193895.2| subtilase family protein [*Arabidopsis thaliana*]
Length=733
Score=1094, P=7.100000e-219
Identities=57%, Positives=72%

10. At1g66220 from *Arabidopsis thaliana*
gi|18408462|ref|NP_564869.1| subtilase family protein [*Arabidopsis thaliana*]
gi|25289828|pir||B96687 subtilisin-like protein, 10849-13974 [imported]—*Arabidopsis thaliana*
gi|12323571|gb|AAG51764.1|subtilisin-like protein; 10849-13974 [*Arabidopsis thaliana*]
Length=753
Score=1080, P=2.400000e-218
Identities=52%, Positives=68%

TABLE 3

| Ortholog Gene Name | Species | GI # | % ID to HIO1004 | Score(s) (BLAST, Clustal, etc.) |
|---|---|---|---|---|
| One EST contig from | *Solanum tubersom* | gi|10446020 | Length: 2156 | TBLASTN |
| | | gi|10446024 | Identities: 0.379 | Score: 1055 |
| | | gi|13612262 | Positives: 0.543 | Probability: 1.700000e-107 |

TABLE 3-continued

| Ortholog Gene Name | Species | GI # | % ID to HIO1004 | Score(s) (BLAST, Clustal, etc.) |
|---|---|---|---|---|
| potato | | gi|13613712<br>gi|14264360<br>gi|14267180<br>gi|15185273<br>consensus:<br>SEQ ID NO: 3 | Frames: 1 | |
| One EST from sugar beet | Beta vulgaris | gi|10711340 | Length: 618<br>Identities: 0.478<br>Positives: 0.652<br>Frames: 3 | TBLASTN<br>Score: 510<br>Probability: 3.000000e-49 |
| One EST contig from soybean | Glycine max | gi|14150445<br>gi|13478114<br>gi|26057369<br>consensus:<br>SEQ ID NO: 6 | Length: 2401<br>Identities: 0.376<br>Positives: 0.562<br>Frames: 1 | TBLASTN<br>Score: 872<br>Probability: 2.100000e-137 |
| One EST from wheat | Triticum aestivum | gi|14313023<br>gi|14313024<br>gi|14313383<br>gi|14313807<br>gi|14314440<br>gi|14314549<br>gi|14316759<br>gi|14316760<br>gi|14317648<br>gi|15315409<br>gi|15772265<br>gi|19956142<br>gi|20048856<br>gi|20086046<br>gi|25157476<br>gi|25218457<br>gi|25238573<br>gi|32559310<br>consensus:<br>SEQ ID NO: 9 | Length: 2564<br>Identities: 0.481<br>Positives: 0.652<br>Frames: 2 | TBLASTN<br>Score: 892<br>Probability: 1.100000e-151 |
| One EST contig from tomato | Lycopersicon esculentum | gi|6536422<br>gi|6536423<br>gi|6536424<br>gi|6536425<br>gi|1771159<br>gi|1771159<br>gi|1771160<br>consensus:<br>SEQ ID NO:4 | Length: 2689<br>Identities: 0.380<br>Positives: 0.554<br>Frames: 2 | TBLASTN<br>Score: 1231<br>Probability: 5.100000-126 |
| One EST contig from rice | Oryza sativa | gi|9453866 | Length: 3026<br>Identities: 0.348<br>Positives: 0.496<br>Frames: 1 | TBLASTN<br>Score: 912<br>Probability: 1.700000e-92 |
| One EST contig from corn | Zea mays | gi|6827742<br>gi|21208160<br>gi|12045659<br>gi|18164698<br>gi|29130115<br>consensus:<br>SEQ ID NO: 7 | Length: 1444<br>Identities: 0.404<br>Positives: 0.574<br>Frames: 1 | TBLASTN<br>Score: 544<br>Probability: 5.000000e-53 |
| One EST contig from cotton | Gossypium hirsutum | gi|5049444<br>gi|5049221<br>gi|5048791<br>gi|5046192<br>gi|5046014<br>gi|5045524<br>consensus:<br>SEQ ID NO: 8 | Length: 1279<br>Identities: 0.360<br>Positives: 0.525<br>Frames: 1 | TBLASTN<br>Score: 592<br>Probability: 8.100000e-59 |
| One EST contig from poplar | Populus tremula | gi|3852817<br>gi|3854402<br>gi|18012433<br>gi|23988298<br>gi|23991758<br>gi|24099801<br>gi|27419447<br>gi|27419568<br>gi|27419599<br>gi|27419823<br>gi|27420015<br>gi|27420028 | Length: 2451<br>Identities: 0.395<br>Positives: 0.554<br>Frames: 3 | TBLASTN<br>Score: 766<br>Probability: 2.700000e-125 |

TABLE 3-continued

| Ortholog Gene Name | Species | GI # | % ID to HIO1004 | Score(s) (BLAST, Clustal, etc.) |
|---|---|---|---|---|
| | | gi\|27420265 | | |
| | | gi\|33183186 | | |
| | | gi\|33183327 | | |
| | | gi\|33184237 | | |
| | | gi\|33185612 | | |
| | | consensus: | | |
| | | SEQ ID NO: 5 | | |

TABLE 4

Closest plant homologs:

| | | | | |
|---|---|---|---|---|
| At4g10550 | *Arabidopsis thaliana* | gi\|18413353 gi\|22136594 | Identities = 98%, Positives = 98% Frames: N | BLASTP Score: 4003 P = 0.000000e+00 |
| At4g10540 | *Arabidopsis thaliana* | gi\|18413351 gi\|7435678 gi\|4539414 gi\|7267751 | Identities = 81%, Positives = 88% Frames: N | BLASTP Score: 3342 P = 0.000000e+00 |
| At4g10510 | *Arabidopsis thaliana* | gi\|18413345 gi\|7435679 gi\|4539411 gi\|7267748 | Identities = 82%, Positives = 89% Frames: N | BLASTP Score: 3244 P = 0.000000e+00 |
| At1g32950 | *Arabidopsis thaliana* | gi\|30692782 | Identities = 76%, Positives = 85% Frames: N | BLASTP Score: 3123 P = 0.000000e+00 |
| At1g32940 | *Arabidopsis thaliana* | gi\|18398655 gi\|25289835 gi\|6910573 gi\|18377745 gi\|29824343 | Identities = 75%, Positives = 85% Frames: N | BLASTP Score: 3100 P = 0.000000e+00 |
| At1g32960 | *Arabidopsis thaliana* | gi\|30692785 gi\|25289832 gi\|6910571 gi\|20466548 gi\|34098815 | Identities = 74%, Positives = 84% Frames: N | BLASTP Score: 3053 P = 2.700000e-317 |
| At1g32970 | *Arabidopsis thaliana* | gi\|15223351 gi\|25289833 gi\|6910574 | Identities = 67%, Positives = 80% Frames: N | BLASTP Score: 2021 P = 3.600000e-237 |
| At4g21650 | *Arabidopsis thaliana* | gi\|30685518 gi\|27311663 | Identities = 56%, Positives = 71% Frames: N | BLASTP Score: 2187 P = 9.600000e-226 |
| At4g21640 | *Arabidopsis thaliana* | gi\|42567017 | Identities = 57%, Positives = 72% Frames: N | BLASTP Score: 1094 P = 7.100000e-219 |
| At1g66220 | *Arabidopsis thaliana* | gi\|18408462 gi\|25289828 gi\|12323571 | Identities = 52%, Positives = 68% Frames: N | BLASTP Score: 1080 P = 2.400000e-218 |

At4g10550 has a N-terminus signal peptide (Max cleavage site probability: 0.232 between pos. 25 and 26 by SignalP) and lacks transmembrane domain (predicted by TMHMM—the predicted transmembrane at the N terminus amino acid residues 7-26 is highly likely to be the signal peptide). This conclusion is supported by the Beers, et al., reference, Phytochemistry 2004, 65:43-58.

Pfam analysis showed that At4g10550 is a member of the subtilisin serine protease family (PF00082, COG1404).

| Model | Domain | seq-f* | seq-t | hmm-f | hmm-t | score | E-value |
|---|---|---|---|---|---|---|---|
| PF05922 | 1/1 | 33 | 113 . . . | 1 | 102 [ ] | 110.8 | 5.1e-30 |
| PF00082 | 1/1 | 127 | 603 . . . | 1 | 349 [ ] | 63.4 | 9.9e-16 |
| COG1404 | 1/1 | 135 | 682 . . . | 1 | 380 [ ] | 54.5 | 4.6e-13 |
| PF02225 | 1/1 | 380 | 483 . . . | 1 | 111 [ ] | 82.3 | 2e-21 |

*Seq-f refers to "sequence-from" and seq-t refers to "sequence-to." The two periods following the seq-t number indicate that the matching region was within the sequence and did not extend to either end. The two brackets indicate that the match spanned the entire length of the profile HMM. hmm-f and hmm-t refer to the beginning and ending coordinates of the matching portion of the profile HMM.

At4g10550 also contains a Subtilisin N-terminal Region (PF05922) and the PA (Protease associated, PF02225) domain. The subtilisin N-terminal region (PF05922, propeptide, also known as inhibitor or activation peptides) functions to inhibit the activity of the protease on which it is present.

Removal of the N-terminal inhibitor domain either by interaction with a second peptidase or by autocatalytic cleavage activates the inactive peptidase (pro-enzyme or zymogen). The propeptide docks into the enzyme moiety shielding the substrate binding site, thereby promoting inhibition of the enzyme. Several such propeptides share a similar topology, despite often low sequence identities. The propeptide region has an open-sandwich antiparallel-alpha/antiparallel-beta fold, with two alpha-helices and four beta-strands with a (beta/alpha/beta)×2 topology. This group of sequences contains the propeptide domain at the N terminus of peptidases belonging to MEROPS family S8A, subtilisins (Rawlings ND, et al., MEROPS: the peptidase database. Nucleic Acids Res. 2004. 32 Database issue: D160-164).

The PA (PF02225; Protease associated) domain is found as an insert domain in diverse proteases, and is thought to mediate protein-protein interaction between protease and substrate (Mahon P, et al., Protein Sci. 2000. 10:1930-1934).

Subtilases (PF00082) are a family of serine proteases. They have independently and convergently evolved an Asp/Ser/His catalytic triad, like that found in the trypsin serine proteases. Peptidases are grouped into clans and families. Clans are groups of families for which there is evidence of common ancestry. Families are grouped by their catalytic type, the first character representing the catalytic type: S, serine; T, threonine; C, cysteine; A, aspartic; M, metallo and U, unknown. A clan that contains families of more than one type is described as being of type P. The serine, threonine and cysteine peptidases utilize the catalytic part of an amino acid as a nucleophile and form an acyl intermediate—these peptidases can also readily act as transferases. In the case of aspartic and metallopeptidases, the nucleophile is an activated water molecule.

Proteolytic enzymes that exploit serine in their catalytic activity are ubiquitous, being found in viruses, bacteria and eukaryotes (Rawlings N. D., Barrett A. J. Families of Serine Peptidases. Meth. Enzymol. 244: 19-61 (1994)). They include a wide range of peptidase activity, including exopeptidase, endopeptidase, oligopeptidase and omega-peptidase activity. Over 20 families (denoted S1-S27) of serine protease have been identified, these being grouped into 6 clans (SA, SB, SC, SE, SF and SG) on the basis of structural similarity and other functional evidence (Rawlings N. D., et al., Meth. Enzymol. 244: 19-61 (1994). Structures are known for four of the clans (SA, SB, SC and SE): these appear to be totally unrelated, suggesting at least four evolutionary origins of serine peptidases and possibly many more (Id.).

Notwithstanding their different evolutionary origins, there are similarities in the reaction mechanisms of several peptidases. Chymotrypsin, subtilisin and carboxypeptidase C clans have a catalytic triad of serine, aspartate and histidine in common: serine acts as a nucleophile, aspartate as an electrophile, and histidine as a base (Id.). The geometric orientations of the catalytic residues are similar between families, despite different protein folds (Id.).

The linear arrangements of the catalytic residues commonly reflect clan relationships. For example the catalytic triad in the chymotrypsin clan (SA) is ordered HDS, but is ordered DHS in the subtilisin clan (SB) and SDH in the carboxypeptidase clan (SC) [Rawlings N. D., et al, Biochem. J. 290: 205-218 (1993)]. This group of serine peptidases belong to the MEROPS peptidase families S8 (subfamilies S8A (subtilisin) and S8B (kexin)) and S53 (sedolisin) both of which are members of clan SB.

The subtilisin family is the second largest serine protease family characterized to date. Over 200 subtilises are presently known, more than 170 of which with their complete amino acid sequence [Siezen R. J., et al., Protein Sci. 6: 501-523 (1997).]. It is widespread, being found in eubacteria, archaebacteria, eukaryotes and viruses (Rawlings N. D., et al., Meth. Enzymol. 244: 19-61 (1994)). The vast majority of the family members are endopeptidases, although there is an exopeptidase, tripeptidyl peptidase (Rawlings N. D., et al., Meth. Enzymol. 244: 19-61 (1994) and Rawlings N. D., et al., Biochem. J. 290: 205-218 (1993). Structures have been determined for several members of the subtilisin family: they exploit the same catalytic triad as the chymotrypsins, although the residues occur in a different order (HDS in chymotrypsin and DHS in subtilisin), but the structures show no other similarity. Some subtilisins are mosaic proteins, and others contain N- and C-terminal extensions that show no sequence similarity to any other known protein. Based on sequence homology, a subdivision into six families has been proposed.

It has been shown that there are 54 subtilisin-like proteases in *Arabidopsis*. Detailed phylogenetic analysis of proteases from *Arabidopsis* showed that At4g10550 is a member of the S8-1 serine protease of which there are 39 members (Eric P Beers, Alan M Jones, Allan W Dickerman. Phytochemistry 2004, 65:43-58). It was shown that At4g10550 is closely related to At4g10540, At4g10510, At1g32940, At1g32950 and At1g32960.

In plants, it has been shown that subtilisin like serine protease may be up-regulated in response to pathogen attack (Jorda L, Vera P. (2000) Plant Physiol 124, 1049-1058), lateral root development (Neuteboom L W, et al., (1999) DNA Res 1999 6, 13-19), and development of root nodule in legumes (Ribeiro A, et al., (1995) Plant Cell 7, 785-794). It has been proposed that these enzymes are not only involved in degradation of extracellular matrix, but also involved in processing proteins that may be part of the cell wall-like matrix or in processing another protein with unknown function (Neuteboom L W, et al (1999) DNA Res 1999 6, 13-19) and Ribeiro A, et al., (1995) Plant Cell 7, 785-794). In addition, it has been suggested that since the ubiquitin/26S proteasome pathway is important to different aspects of plant biology, proteases may play diverse functions in planta (Beers, et al, Phytochemistry 2004, 65:43-58). It has been shown that some predicted serine proteases possess acyltransferase instead of hydrolase (Id.).

Example 5

Transformed explants of rapeseed, soy, corn, sunflower, cotton, cocoa, safflower, oil palm, coconut palm, flax, castor and peanut are obtained through *Agrobacterium tumefaciens*-mediated transformation or microparticle bombardment. Plants are regenerated from transformed tissue. The greenhouse grown plants are then analyzed for the gene of interest expression levels as well as oil levels.

Example 6

This example provides analytical procedures to determine oil and protein content, mass differences, amino acid composition, free amino acid levels, and micronutrient content of transgenic maize plants.

Oil levels (on a mass basis and as a percent of tissue weight) of first generation single corn kernels and dissected germ and endosperm are determined by low-resolution $^1$H nuclear magnetic resonance (NMR) (Tiwari et al., *JAOCS,* 51:104-109 (1974); or Rubel, *JAOCS,* 71:1057-1062 (1994)), whereby NMR relaxation times of single kernel samples are measured, and oil levels are calculated based on regression analysis using a standard curve generated from analysis of corn kernels with varying oil levels as determined gravimetrically following accelerated solvent extraction. One-way analysis of variance and the Student's T-test (JMP, version 4.04, SAS Institute Inc., Cary, N.C., USA) are performed to identify significant differences between transgenic and non-transgenic kernels as determined by transgene-specific PCR.

Oil levels and protein levels in second generation seed are determined by NIT spectroscopy, whereby NIT spectra of pooled seed samples harvested from individual plants are measured, and oil and protein levels are calculated based on regression analysis using a standard curve generated from analysis of corn kernels with varying oil or protein levels, as determined gravimetrically following accelerated solvent extraction or elemental (% N) analysis, respectively. One-way analysis of variance and the Student's T-test are performed to identify significant differences in oil (% kernel weight) and protein (% kernel weight) between seed from marker positive and marker negative plants.

The levels of free amino acids are analyzed from each of the transgenic events using the following procedure. Seeds from each of the transgenic plants are crushed individually into a fine powder and approximately 50 mg of the resulting powder is transferred to a pre-weighed centrifuge tube. The exact sample weight is recorded and 1.0 ml of 5% trichloroacetic acid is added to each sample tube. The samples are mixed at room temperature by vortex and then centrifuged for 15 minutes at 14,000 rpm on an Eppendorf microcentrifuge (Model 5415C, Brinkmann Instrument, Westbury, N.Y.). An aliquot of the supernatant is removed and analyzed by HPLC (Agilent 1100) using the procedure set forth in Agilent Technical Publication "Amino Acid Analysis Using the Zorbax Eclipse-AAA Columns and the Agilent 1100 HPLC," Mar. 17, 2000.

Quantitative determination of total amino acids from corn is performed by the following method. Kernels are ground and approximately 60 mg of the resulting meal is acid-hydrolyzed using 6 N HCl under reflux at 100° C. for 24 hrs. Samples are dried and reconstituted in 0.1 N HCl followed by precolumn derivatization with α-phthalaldehyde (OPA0 for HPLC analysis. The amino acids are separated by a reverse-phase Zorbax Eclipse XDB-C 18 HPLC column on an Agilent 1100 HPLC (Agilent, Palo Alto, Calif.). The amino acids are detected by fluorescence. Cysteine, proline, asparagine, glutamine, and tryptophan are not included in this amino acid screen (Henderson et al., "Rapid, Accurate, Sensitive and Reproducible HPLC Analysis of Amino acids, Amino Acid Analysis Using Zorbax Eclipse-AAA Columns and the Agilent 1100 HPLC," Agilent Publication (2000); see, also, "Measurement of Acid-Stable Amino Acids," AACC Method 07-01 (American Association of Cereal Chemists, Approved Methods, 9th edition (LCCC# 95-75308)). Total tryptophan is measured in corn kernels using an alkaline hydrolysis method as described (Approved Methods of the American Association of Cereal Chemists—10$^{th}$ edition, AACC ed, (2000) 07-20 Measurement of Tryptophan—Alakline Hydrolysis).

Tocopherol and tocotrienol levels in seeds are assayed by methods well-known in the art. Briefly, 10 mg of seed tissue are added to 1 g of microbeads (Biospec Product Inc, Barlesville, Okla.) in a sterile microfuge tube to which 500 µl 1% pyrogallol (Sigma Chemical Co., St. Louis, Mo.)/ethanol have been added. The mixture is shaken for 3 minutes in a mini Beadbeater (Biospec) on "fast" speed, then filtered through a 0.2 µm filter into an autosampler tube. The filtered extracts are analyzed by HPLC using a Zorbax silica HPLC column (4.6 mm×250 mm) with a fluorescent detection, an excitation at 290 nm, an emission at 336 nm, and bandpass and slits. Solvent composition and running conditions are as listed below with solvent A as hexane and solvent B as methyl-t-butyl ether. The injection volume is 20 µl, the flow rate is 1.5 ml/minute and the run time is 12 minutes at 40° C. The solvent gradient is 90% solvent A, 10% solvent B for 10 minutes; 25% solvent A, 75% solvent B for 11 minutes; and 90% solvent A, 10% solvent B for 12 minutes. Tocopherol standards in 1% pyrogallol/ethanol are run for comparison (α-tocopherol, γ-tocopherol, β-tocopherol, δ-tocopherol, and tocopherol (tocol)). Standard curves for alpha, beta, delta, and gamma tocopherol are calculated using Chemstation software (Hewlett Packard). Tocotrienol standards in 1% pyrogallol/ethanol are run for comparison (α-tocotrienol, γ-tocotrienol, β-tocotrienol, δ-tocotrienol). Standard curves for α-, β-, δ-, and γ-tocotrienol are calculated using Chemstation software (Hewlett Packard).

Carotenoid levels within transgenic corn kernels are determined by a standard protocol (Craft, *Meth. Enzymol.*, 213: 185-205 (1992)). Plastiquinols and phylloquinones are determined by standard protocols (Threlfall et al., *Methods in Enzymology*, XVIII, part C, 369-396 (1971); and Ramadan et al., *Eur. Food Res. Technol.*, 214(6):521-527 (2002)).

REFERENCES

Altschul, S. F. et al., J. Mol. Biol. 215:403-410, 1990.

Altschul, S. F. et al., Nucleic Acids Res. 25:3389-3402, 1997.

Ausubel F M et al., Current Protocols in Molecular Biology, John Wiley & Sons, New York, N.Y., 1993.

Baldwin D et al., Cur Opin Plant Biol. 2(2):96-103, 1999.

Bateman et al., 1999, Nucleic Acids Res 27:260-262 (website at pfam.wustl.edu).

Baulcombe D, Arch Virol Suppl 15:189-201, 1999.

Cannon et al., Plant Molec. Biol. (1990) 15:39-47.

Ch'ng et al., Proc. Natl. Acad. Sci. USA (1989) 86:10006-10010

Christensen S et al., 9$^{th}$ International Conference on *Arabidopsis* Research. Univ. of Wisconsin-Madison, Jun. 24-28, 1998. Abstract 165.

Christou et al., Proc. Natl. Acad. Sci USA (1989) 86:7500-7504.

De Block et al., Plant Physiol. (1989) 91:694-701.

Dieffenbach C and Dveksler G (Eds.) PCR Primer: A Laboratory Manual, Cold Spring Harbor Laboratory Press, NY, 1989.

Everett et al., Bio/Technology (1987) 5:1201

Feldmann et al., Science 243: 1351-1354, 1989.

Focks N and Benning C, Plant Physiol 118:91-101, 1998.

Fridborg I et al., Plant Cell 11: 1019-1032, 1999.

Harlow E and Lane D, Antibodies: A Laboratory Manual, Cold Spring Harbor Laboratory Press, 1988, New York.

Harlow E and Lane D, Using Antibodies: A Laboratory Manual, Cold Spring Harbor Laboratory Press, 1999, New York Hayashi H et al., Science 258: 1350-1353, 1992.

Jako et al., Plant Physiology 126(2):861-74, 2001.

James D W and Dooner H K (1990) Theor Appl Genet 80, 241-245.

Jones J D et al., Transgenic Res 1:285-297 1992.

Kardailsky I et al., Science 286: 1962-1965, 1999.

Katavic V et al., Plant Physiology 108(1):399-409, 1995.

Kline et al., Nature (1987) 327:70.

Kunkel T A et al., Methods Enzymol. 204:125-39, 1991.

Lemieux B., et al., 1990, Theor Appl Genet 80, 234-240.

Nakamura Y et al., 1999, Nucleic Acids Res 27:292.

Napoli, et al., Plant Cell 2:279-289, 1990.
Okuley et al., Plant Cell 6(1):147-158, 1994.
Sambrook et al., Molecular Cloning: A Laboratory Manual (Second Edition), Cold Spring Harbor Press, Plainview, N.Y., 1989.
Schaffer R, et al., Cell 93: 1219-1229, 1998.
Sheehy et al., Proc. Natl. Acad. Sci. USA (1988) 85:8805-8809.
Smith, et al., Nature 334:724-726, 1988.
Smith et al., Mol. Gen. Genetics (1990) 224:477-481.
Thompson J D et al., Nucleic Acids Res 22:4673-4680, 1994.
van der Krol et al., Biotechniques (1988) 6:958-976.
van der Krol et al., The Plant Cell (1990) 2:291-299.
Van Haaren M J J et al., Plant Mol Bio 21:625-640, 1993.
Verdaguer B et al., Plant Mol Biol 37:1055-1067, 1998.
Waterhouse, et al., Proc. Natl. Acad. Sci. USA 95:13959-13964, 1998.
Weigel D, et al., Plant Physiology, 122:1003-1013, 2000.
Wilson K et al., Plant Cell 8: 659-671, 1996.
Yadav N S et al., (1993) Plant Physiol 103, 467-476.
Beers, et al., Phytochemistry 2004, 65:43-58.
Rawlings N D, et al., Nucleic Acids Res. 2004. 32 Database issue: D160-164
Mahon P, Bateman A. Protein Sci. 2000. 10:1930-1934.
Rawlings N. D., et al, Meth. Enzymol. 244: 19-61 (1994)
Rawlings N. D., et al, Biochem. J. 290: 205-218 (1993)
Siezen R. J., et al., Protein Sci. 6: 501-523 (1997).
Jorda L, et al., Plant Physiol 124, 1049-1058 (2000).
Neuteboom L W, et al., DNA Res 1999 6, 13-19.
Ribeiro A, et al., Plant Cell 7, 785-794 (1995).

It is claimed:

1. A transgenic plant comprising a plant transformation vector comprising a nucleotide sequence that encodes a polypeptide comprising an amino acid sequence having at least 95% sequence identity to the amino acid sequence of SEQ ID NO:2, whereby the transgenic plant has a high oil phenotype relative to a plant of the same species not comprising the plant transformation vector.

2. The transgenic plant of claim 1, which is selected from the group consisting of rapeseed, soy, corn, sunflower, cotton, cocoa, safflower, oil palm, coconut palm, flax, castor and peanut.

3. A plant part obtained from the plant according to claim 1, wherein said plant part comprises said plant transformation vector.

4. The plant part of claim 3, which is a seed.

5. A method of producing oil comprising growing the transgenic plant of claim 1 and recovering oil from said transgenic plant.

6. The method of claim 5, wherein the oil is recovered from a seed of the plant, wherein said seed comprises said plant transformation vector.

7. A method of producing a high oil phenotype in a plant, said method comprising:
   a) introducing into progenitor cells of the plant a plant transformation vector comprising a nucleotide sequence that encodes a polypeptide comprising an amino acid sequence having at least 95% sequence identity to the amino acid sequence of SEQ ID NO:2, to produce transformed cells overexpressing the polypeptide;
   b) growing the transformed progenitor cells to produce a transgenic plant, wherein said polynucleotide sequence is expressed, and
   c) identifying said transgenic plant that exhibits a high oil phenotype relative to a plant of the same species not comprising the plant transformation vector.

8. A plant obtained by a method of claim 7.

9. The plant of claim 8, which is selected from the group consisting of rapeseed, soy, corn, sunflower, cotton, cocoa, safflower, oil palm, coconut palm, flax, castor and peanut.

* * * * *

SEQUENCE LISTING

```
<160> NUMBER OF SEQ ID NOS: 9

<210> SEQ ID NO 1
<211> LENGTH: 2368
<212> TYPE: DNA
<213> ORGANISM: Arabidopsis thaliana

<400> SEQUENCE: 1
atgatgaatt acagaacatc catatatgtg gtactaagtt tggtaatatt tctcaatgtg      60
cagagaagtt ttgtggcaga atcaagtgct aagagaaagg ttcatatagt gtatttgggt     120
gagaagcaac atgatgatcc tgagtttgtt acggaatctc atcatcggat gttatggtca     180
cttcttggaa gtaaagagga tgccaatgat tcaatggtgt atagttaccg acatggcttc     240
tcaggttttg cggctaaaact taccgagtcc caagccaaga agatagctga tttacctgat     300
gttgttcatg ttataccgga tagtttctat aagctggcaa caactcgaac ttgggattat     360
ctaggccttt ctgctgccaa tccaaagagt cttctacatg aaactaatat gggtgaacaa     420
attatcatcg gtgttataga cacaggagta tggcctgaat ctgaagtatt taatgacagt     480
gggtttgggc ctgtgccaag ccactggaaa ggaggttgtg aaacaggaga gaatttcaac     540
tcctctaact gcaataaaaa gctcatagga gccaagtatt tcatcaatgg ttttctagcg     600
gagaacgaaa gcttcaactc cacaaattca cttgatttca tttccctag agaccttgat      660 ggtcatggca cacatgtttc caccattgcg ggtggttctt tcgtgcccaa tataagctac     720
aagggcttag ctggagggac tgtcagaggc ggggcacctc gtgctcatat agcaatgtac     780
aaggcttgtt ggtatctgga tgatgatgac acaacgactt gttcatctgc tgacatcttg     840
aaagctatgg acgaggctat gcatgatggt gttgatgttc tgtcaatctc tttaggctcc     900
agcgttcctc tatatggtga aactgatatt cgcgatggga taactactgg agcgttccat     960
gcagtcttaa agggtatcac tgttgtttgt tccggtggta actctggccc agattctctt    1020
accgtgacaa acacagctcc ttggatcatc acagtggctg caactactct ggaccggtcc    1080
tttgccacac ctcttacact tgggaataat aaagtgatat gggtcaagc aatgtacaca     1140 ggtccaggac ttggcttcac tagcttggtt tatcctgaga atccagggaa tagcaacgaa    1200 agttttctg gtacttgtga ggagcttta ttcaattcta atcgtacaat ggaggggaaa      1260
gttgtgttgt gtttcacaac atcacctac ggcggtgctg tattaagcgc tgcgcgttat      1320
gtgaagagag caggtggtct tggcgtaatc atcgcaagac acccgggtta cgctatccag    1380
```

-continued

```
ccatgtctag atgatttccc ttgtgttgct gtttgactggg agcttgggac tgatatactt    1440
ctctacacac ggtccagtgg atcgcctgtg gtgaagatac aaccttctaa acacttgta     1500 ggacaaccag ttggtacaaa agtggcaacg ttctcatcaa gagggcctaa ttcgatcgcc    1560
cctgcgattc tcaaaccgga tatagcagca ccgggagtga gcatattggc agctacaacc   1620
aacaccactt tcagcgacca agggttcatt atgttgtctg aacatcaat ggcagctcct    1680 gcaatttcag gagttgctgc acttctcaaa gctctgcacc gtgattggtc tcctgctgcc   1740
attagatcag ccattgtcac tacagcttgg aaaacagatc catttggaga gcagatattt   1800
gctgaagggt cacctccgaa gctagctgat ccgttcgact atggtggagg ccttgtaaat   1860
ccagagaaat ctgcaaatcc aggtcttgta tatgacatgg gcctcgaaga ctatgttctc   1920
tacatgtgct ctgttggtta caacgagaca tcaatctctc agcttatcgg taaacaaca    1980 gtctgttcaa atccgaaacc atctgttctt gatttcaact tgccttccat cacaatccca   2040
aacctcaaag acgaagtgac tatcacaaga actgtcacta cgttggacc tctcaactca    2100 gtctatagag taacggtcga gccacctttg ggttttcaag tgactgtgac accggagacg   2160
ctagtattca actctacgac caaaaaagtc tattttaaag ttaaagtctc aaccacacac   2220
aaaaccaata caggttacta ctttggaagc ttgacatgga gtgactctct gcacaatgtc   2280
accattcctt tgtctgtgag gacgcaaatc ctgcagaact attatgatga aaattaaact   2340
tataaaaatg actaaccatt tgtgtgct                                       2368

<210> SEQ ID NO 2
<211> LENGTH: 778
<212> TYPE: PRT
<213> ORGANISM: Arabidopsis thaliana

<400> SEQUENCE: 2

Met Met Asn Tyr Arg Thr Ser Ile Tyr Val Val Leu Ser Leu Val Ile
1               5                   10                  15

Phe Leu Asn Val Gln Arg Ser Phe Val Ala Glu Ser Ser Ala Lys Arg
            20                  25                  30

Lys Val His Ile Val Tyr Leu Gly Glu Lys Gln His Asp Asp Pro Glu
        35                  40                  45

Phe Val Thr Glu Ser His His Arg Met Leu Trp Ser Leu Leu Gly Ser
    50                  55                  60

Lys Glu Asp Ala Asn Asp Ser Met Val Tyr Ser Tyr Arg His Gly Phe
65                  70                  75                  80

Ser Gly Phe Ala Ala Lys Leu Thr Glu Ser Gln Ala Lys Lys Ile Ala
                85                  90                  95

Asp Leu Pro Asp Val Val His Val Ile Pro Asp Ser Phe Tyr Lys Leu
            100                 105                 110

Ala Thr Thr Arg Thr Trp Asp Tyr Leu Gly Leu Ser Ala Ala Asn Pro
        115                 120                 125

Lys Ser Leu Leu His Glu Thr Asn Met Gly Glu Gln Ile Ile Ile Gly
    130                 135                 140

Val Ile Asp Thr Gly Val Trp Pro Glu Ser Glu Val Phe Asn Asp Ser
145                 150                 155                 160

Gly Phe Gly Pro Val Pro Ser His Trp Lys Gly Gly Cys Glu Thr Gly
                165                 170                 175

Glu Asn Phe Asn Ser Ser Asn Cys Asn Lys Lys Leu Ile Gly Ala Lys
            180                 185                 190

Tyr Phe Ile Asn Gly Phe Leu Ala Glu Asn Glu Ser Phe Asn Ser Thr
```

```
            195                 200                 205
Asn Ser Leu Asp Phe Ile Ser Pro Arg Asp Leu Asp Gly His Gly Thr
    210                 215                 220

His Val Ser Thr Ile Ala Gly Gly Ser Phe Val Pro Asn Ile Ser Tyr
225                 230                 235                 240

Lys Gly Leu Ala Gly Thr Val Arg Gly Ala Pro Arg Ala His
                245                 250                 255

Ile Ala Met Tyr Lys Ala Cys Trp Tyr Leu Asp Asp Asp Thr Thr
            260                 265                 270

Thr Cys Ser Ser Ala Asp Ile Leu Lys Ala Met Asp Glu Ala Met His
        275                 280                 285

Asp Gly Val Asp Val Leu Ser Ile Ser Leu Gly Ser Ser Val Pro Leu
    290                 295                 300

Tyr Gly Glu Thr Asp Ile Arg Asp Gly Ile Thr Thr Gly Ala Phe His
305                 310                 315                 320

Ala Val Leu Lys Gly Ile Thr Val Val Cys Ser Gly Gly Asn Ser Gly
                325                 330                 335

Pro Asp Ser Leu Thr Val Thr Asn Thr Ala Pro Trp Ile Ile Thr Val
            340                 345                 350

Ala Ala Thr Thr Leu Asp Arg Ser Phe Ala Thr Pro Leu Thr Leu Gly
        355                 360                 365

Asn Asn Lys Val Ile Leu Gly Gln Ala Met Tyr Thr Gly Pro Gly Leu
    370                 375                 380

Gly Phe Thr Ser Leu Val Tyr Pro Glu Asn Pro Gly Asn Ser Asn Glu
385                 390                 395                 400

Ser Phe Ser Gly Thr Cys Glu Glu Leu Leu Phe Asn Ser Asn Arg Thr
                405                 410                 415

Met Glu Gly Lys Val Val Leu Cys Phe Thr Thr Ser Pro Tyr Gly Gly
            420                 425                 430

Ala Val Leu Ser Ala Ala Arg Tyr Val Lys Arg Ala Gly Gly Leu Gly
        435                 440                 445

Val Ile Ile Ala Arg His Pro Gly Tyr Ala Ile Gln Pro Cys Leu Asp
    450                 455                 460

Asp Phe Pro Cys Val Ala Val Asp Trp Glu Leu Gly Thr Asp Ile Leu
465                 470                 475                 480

Leu Tyr Thr Arg Ser Ser Gly Ser Pro Val Val Lys Ile Gln Pro Ser
                485                 490                 495

Lys Thr Leu Val Gly Gln Pro Val Gly Thr Lys Val Ala Thr Phe Ser
            500                 505                 510

Ser Arg Gly Pro Asn Ser Ile Ala Pro Ala Ile Leu Lys Pro Asp Ile
        515                 520                 525

Ala Ala Pro Gly Val Ser Ile Leu Ala Ala Thr Thr Asn Thr Thr Phe
    530                 535                 540

Ser Asp Gln Gly Phe Ile Met Leu Ser Gly Thr Ser Met Ala Ala Pro
545                 550                 555                 560

Ala Ile Ser Gly Val Ala Ala Leu Leu Lys Ala Leu His Arg Asp Trp
                565                 570                 575

Ser Pro Ala Ala Ile Arg Ser Ala Ile Val Thr Thr Ala Trp Lys Thr
            580                 585                 590

Asp Pro Phe Gly Glu Gln Ile Phe Ala Glu Gly Ser Pro Pro Lys Leu
        595                 600                 605

Ala Asp Pro Phe Asp Tyr Gly Gly Gly Leu Val Asn Pro Glu Lys Ser
    610                 615                 620
```

```
Ala Asn Pro Gly Leu Val Tyr Asp Met Gly Leu Glu Asp Tyr Val Leu
625                 630                 635                 640

Tyr Met Cys Ser Val Gly Tyr Asn Glu Thr Ser Ile Ser Gln Leu Ile
            645                 650                 655

Gly Lys Thr Thr Val Cys Ser Asn Pro Lys Pro Ser Val Leu Asp Phe
            660                 665                 670

Asn Leu Pro Ser Ile Thr Ile Pro Asn Leu Lys Asp Glu Val Thr Ile
            675                 680                 685

Thr Arg Thr Val Thr Asn Val Gly Pro Leu Asn Ser Val Tyr Arg Val
690                 695                 700

Thr Val Glu Pro Pro Leu Gly Phe Gln Val Thr Val Thr Pro Glu Thr
705                 710                 715                 720

Leu Val Phe Asn Ser Thr Thr Lys Lys Val Tyr Phe Lys Val Lys Val
            725                 730                 735

Ser Thr Thr His Lys Thr Asn Thr Gly Tyr Tyr Phe Gly Ser Leu Thr
            740                 745                 750

Trp Ser Asp Ser Leu His Asn Val Thr Ile Pro Leu Ser Val Arg Thr
            755                 760                 765

Gln Ile Leu Gln Asn Tyr Tyr Asp Glu Asn
770                 775
```

<210> SEQ ID NO 3
<211> LENGTH: 2156
<212> TYPE: DNA
<213> ORGANISM: Artificial sequence
<220> FEATURE:
<223> OTHER INFORMATION: synthetic construct

<400> SEQUENCE: 3

```
gaaaggactg aaaatgagcc aacaactatc tataacgtgg cacaataaag cccatcaaat     60
atctctctta tcttcccaga aactagtgtc tctttagcga tggcactttc ttcttcctct    120
ttctcccccc tagtcttcct ctttctcagc tcattggcaa tttcagtcaa atcggatggt    180
cctaaaactt tcatagtcca cgtgtccata tcccacaagc tcatattttt cactactcac    240
catcattggt actcctctat tctccgatca gtctctcaac actctcccaa tatcttgtat    300
tcttatgatc gtgctgcccg tggcttctct gcccgcctta tcccgggca ggctgaccag    360
ctcagccgcg ttcccggtgt ggtctccgtc atccctgatc gcgtacgcca acttcatacc    420
actcacacac ctaccttctt aggccttgaa gactcatttg ggatttggcc caattctgat    480
tatgctgata atgttattgg tggggtcctt gacacgggta tttggccaga aaggccgagc    540
ttttccgaca aggggctttc gccggtgcct tcaggttgga agggaaatg cgagagtggc    600
ccggactttc ctgcaacttc atgtaatcgt aaaatcatag gtgctagatt gttttacaaa    660
ggatatgaag ctgatcgtgg aagtccaatg gatgaatcta agaatccaa atcgccaaga    720
gatactgaag gccatggaac tcacactgct tcaactgcag ctggatctgt tgtagccaat    780
gcgagctttt accaatatgc aaaaggtgaa gctagaggta tggccgtaaa agctagaata    840
gcagcctata gatctgctg gaaaacaggg tgttttgatt ctgatatact ggctgcaatg    900
gatcaagctg ttgcggacgg ggttcacgtg atttctctct ctgttggcgc agatggttat    960
tctcctgagt atgacgttga ctccattgct attggagctt tggtgccac agaacatggc   1020
gttgtcgtct cttgctctgc tggaaattcc ggtcctggtg cttctacggc ggtcaacgtt   1080
gccccatgga ttctcactgt tgctgcttca accatagatc gggagtttcc agcggatgtt   1140
```

```
atcttaggag acggtagaat atttggtggt gtatccttat ataccggaga tccccttggc    1200
aatgcaaaac tacagcttgt ttattccgcc gactgtggca gccaactctg ttatccagga    1260
aagctggacc cttcaaaagt tgctgggaaa attgtattat gtgatcgagg aggcaatgcc    1320
agagtagaga aggaagtgc tgtgaaacaa gcgggcggtg caggtatggt cctagcaaac    1380
ttagctgact ctggagaaga actcgttgcc gatgcacatc tcctcccagc gaccatggtg    1440
ggtcaaaaag ctggcaataa atcagggat tacatcaaat ctgttccatc accaacagcg    1500
acgatcactt tcaagggaac tgttatagga aaatcgccat ctgctccacg cattgctgcg    1560
ttctcaggcc gaggacccaa ttatgtgacc cctgagatcc ttaaaccgga cgttactgca    1620
ccgggagtca acatattagc tggatggacc ggagctgttg gtccaacaga cttggaaatc    1680
gacaaaagaa gagtggaatt caacattata tccgggacat ccatgtcttg tcctcatgta    1740
agtggattag ctgcgttact cagaaaggct tatcctaaat ggaccacagc agccataaaa    1800
tcagccctca tgacaacagc ttacaacgtt gacaactccg gcaaaacaat cacggatctt    1860
gccacaggtc aagaatcgag tcctttcgtt cgtgggtcgg acatgtgga tccaaacaga    1920 gcactgcatc cgggtctggt ttacgacatt gagtcgagtg attacgtagg tttcctatgc    1980
gccattggtt atggcccctc cagaatctca ccattcacga agatacttc ttcagtgaat    2040 tgcagtgaac atagtttggc tagtccaggg gatttgaatt atccatcatt ctcagttgtt    2100
ttcatgagtg agaatgttgt gaaatacaag cgtgtggtta aaaatgttgg gaggaa        2156
```

<210> SEQ ID NO 4
<211> LENGTH: 2689
<212> TYPE: DNA
<213> ORGANISM: Artificial sequence
<220> FEATURE:
<223> OTHER INFORMATION: synthetic construct

<400> SEQUENCE: 4

```
ctagcattac atatcatagt cagttagagc ctatcactca aaactccagc ccatctccac      60
cacaggagga aaaaaaaaaa agcttttctt ttcagtagag atttaacttt caccttcgac     120
actaagaact cacataaaga tggaaagact caggctcatg tttcttttaa tactaatggt     180
agtgttgttt catgtgtttg ttgatgcaag acagaaccag aagaagactt atataattca     240
catggacaag ttcaacatgc ctgctgattt tgatgatcat actcagtggt atgactcatc     300
attgaagtca gtatccaaga gcgccaacat gctttacacc tacaacagtg tcatccatgg     360
ctactcaaca cagctaacag ctgatgaagc caaagcactt gcacagcaac cgggaattct     420
cttggtccac gaggaagtga tatacgagct tcacaccact cgatcccta cgtttctggg     480 acttgaagga cgtgaaagta gatcattctt tcctcagact gaagcaagga gtgaggtcat     540
tattggtgtg ctggacacag gtgtttggcc tgaatcaaaa agttttgatg acactggact     600
aggtcaagtc cctgcgagct ggaagggtaa gtgtcaaact ggcaagaact tcgacgcatc     660
aagctgtaat cggaaactta ttggtgcgag ttttctctca caaggttatg aagcagcttt     720 tgggcaatc gatgagacca ttgaatccaa gtcaccaagg gacgatgaag ccatggcac     780 acacactgca actacagcag ctggctcggt tgtaaccgga gctagcctct gggttatgc     840 aactggtaca gcacgtggga tggcttcaca cgcaagggtg gcagcgtaca aggtatgttg     900
gaccggagga tgtttagca gcgacatact ggcagggatg gaccaggctg tcatagatgg     960
tgtaaatgtg ctctcactgt cccttggtgg cacaatttct gattatcata gggacatagt    1020
tgcaatcgga gcattttctg cagcatctca agggatcttt gtctcatgct cagcggggaa    1080
```

```
tggtggtcca agctctggga cgctatccaa cgttgcacca tggataacta ctgtaggtgc    1140
tggaaccatg gaccgtgaat tccagcata cattggcatt ggaaatggga aaaaactcaa    1200
tggagtatca ctttacagtg gaaaggcatt gcctagttct gtgatgccac tggtgtatgc    1260
tggaaatgtc agccaatcat ctaatggaaa tttatgcacc agtggtagtc taattccaga    1320
aaaagttgct ggaaaaattg tcgtctgtga ccggggatg aatgcaaggg cacaaaaggg     1380
tttggttgtg aaggatgctg gtggaatagg gatgattctg gcaaacacag acacttacgg    1440
agatgagttg gttgctgatg cacacctcat acctacagct gcagttggtc aaactgcggg    1500
caacttgatc aagcagtaca tagcttctaa cagcaatcca actgccacaa ttgcatttgg    1560
aggaaccaag ttgggtgttc aaccatcgcc agttgttgca gcttttagtt ccagagggcc    1620
aaacccaatc acaccagatg tactcaaacc tgatttgata gcaccaggtg tcaatattct    1680
tgctggctgg acagggaaag ttggaccaac tggcttgcaa gagacaccag gaatgtagg    1740 cttcaacatc atctctggaa cttccatgtc atgtccccat gtaagtgggc tagcagcact    1800
actcaaagct gcccatccag aatggagtcc agcagctata aggtcagcac tgatgactac    1860
aagttatagc acatacaaaa acggaaaaac aatcgaggat gttgcaacag gaatgtcatc    1920
tacaccattt gattatggtg ctggacatgt gaatccaaca gcagctgtca gtcctggttt    1980
agtgtatgat ctaacagttg atgactatat aaactttcta tgtgccttgg actacagccc    2040
gagtatgatc aaggtcattg caaaaagaga catctcctgt gacgaaaata aggagtatag    2100
agttgctgat cttaattacc catcttttc cattcctatg gaaacggcct ggggtgaaca    2160
tgcagatagt agtaccccca ccgtgaccag atacacaagg actctaacaa atgtgggaaa    2220
cccagctaca tacaaggcct cagtctcttc tgaaacacag gacgtgaaga ttctggttga    2280
gccacaaaca cttactttca gccgaaagaa cgaaagaaa acctacactg tgacattcac    2340
tgctacttcc aagccatcag gcacaaccag cttcgctcga ctggagtggt cagatggaca    2400
acacgttgtt gcaagcccaa ttgctttcag ctggacatga ttctgctagt tctaagtcat    2460
tcaccacaaa tgtacaagtg ctaatagtcc tttttaaata attactagtg tgcagcagtt    2520
actcctctaa tatttcacca actgaacaag tatcctgacc tataattaag aagcctaggc    2580
aattctaggc aatgttggtt gatttgccca gcaaaaggct ggtgctgtat ttgccagata    2640
taattatgta ctgaaccaca caatacaggt ggatattatt tggctttt                 2689
```

<210> SEQ ID NO 5
<211> LENGTH: 2453
<212> TYPE: DNA
<213> ORGANISM: Artificial sequence
<220> FEATURE:
<223> OTHER INFORMATION: synthetic construct
<220> FEATURE:
<221> NAME/KEY: misc_feature
<222> LOCATION: (729)..(729)
<223> OTHER INFORMATION: n is a, c, g, or t
<220> FEATURE:
<221> NAME/KEY: misc_feature
<222> LOCATION: (2397)..(2397)
<223> OTHER INFORMATION: n is a, c, g, or t

<400> SEQUENCE: 5

```
accgttgatc aaccctacaa aacctacatc attcgcattg actctcaatc caagccctcc      60
attttcccca ctcactacaa ctggtacacc actgaattca ctagcacccc acaaatcctc     120
cacacttacg acaccgtttt ccatggcttc tccgccatac taacaccaga ccgcgccgcc     180
```

```
actctcagcc aacacccatc agtcctcgcc gtgatcgaag atcaacggaa acaactccac    240
accactcggt ctcctcagtt tcttggactc agaaaccaac gtggtctctg gtcggattct    300
gattatggtt ctgatgttat cattggcgtt ctcgataccg ggatctggcc agaacgacgg    360
agcttctctg acgtcaatct tggagcgatt cctgctcggt ggaaaggaat tgtgaagtc     420 ggtgaaagat tttcagcaag aaactgcaac aagaagttga ttggtgcccg gttttttatc    480
aaaggacatg aggcagcaag tgggagcacg ggaccgatta ctcctataaa tgaaactgtg    540
gagtttaagt ctccacgaga tgccgatggt catgggactc acacggcatc aaccgcggca    600
ggaaggcatg catttcgtgc tagcatggaa ggttttgcag cggggattgc gaaagggta    660 gctccgaaag cacgtttggc tgtgtataaa gtttgctgga agaatgcagg atgttttgat    720
tctgatatnt tagctgcttt tgatgctgcg gttaaagatg gagttgatgt catttcgatt    780
tccattggtg gtggtgatgg gatttcggca ccttattatc ttgatccgat tgccatcggt    840
gcttatggtg cggcttctag aggggttttt gtctcgtctt cggctgggaa tgacgggcct    900
aatttaatgt cagtgacgaa tcttgctccg tggattgtta ctgttggtgc tggaacaatt    960
gacaggaatt cccccgcaga agttgttctt ggtaatggga agagattatc tggtgtttcg   1020
ctatatgctg gtttgccatt gagtggtaaa atgtatcctc tggtttatcc ggggaaatca   1080
ggggttttgt cttcgtcact gtgtatggaa agttcattgg atcctaatat ggtgaaggga   1140
aaaattgttg tttgcgatcg cggaagtagc gcaagagtgg caaaagggtt ggttgttaag   1200
aaagctggag tgttggtat gattcttgct aatggaattt ctaatggtga aggtttagtt    1260
ggcgatgctc atttaattcc tacctgtgct cttggttctg atgagggtga tacagtcaag   1320
gcttatgttt cagccacttc gaatccggtt gctactattg ctttcaaagg tactgtgatc   1380
ggaatcaaac cagctcctgt tgtggcttcg ttttcgggta gggggccaaa tggattgacc   1440
ccggagattc tgaagccgga cttgatcgct cctggggtga acattcttgc tgcttggacg   1500
gatgctgttg gtccaactgg attggattca gatactcgaa aaactgaatt caacattctt   1560
tcaggcactt caatggcatg tcctcatgta agtggcgccg cagccttgct taaatctgcc   1620
cacccagatt ggagtccggc agcaattagg tctgcaatga tgaccactgc caatacattc   1680
aataatctaa accagtcaat gactgacgag gccactggaa acgtgtcgtc atcatacgat   1740
ttgggtgcag ggcatctcaa tcttgatcga gcaatggatc cagggttggt ttatgatatt   1800
accaacaacg attatgtgaa ctttttgtgt ggaattggat acgggcctag agtaattcag   1860
gtgatcacgc gatcaccagt gagttgtcta gagaagaaac cattgccaga gaacctcaat   1920 taccottcaa tcgcagcatt gcttccgagc tcagcaaagg gagcaacaag caaggcattc   1980
atcagaacag tcaccaatgt gggtcaaccg gacgctgttt atcgtttcac aatccaagct   2040
ccaaaagggg tcacagtgac agtgaaacca ccacaattgg tgttcaccga ggccgtgaag   2100
aagcagagct tcattgtaac cataacggcc aacacccgga atctgatgct ggatgattcg   2160
ggtgctgtat tcgggtccac tttcgtggtc tgacgggaag catgtcgtta ggagtcccat   2220
tttggtgacc cagatagatc ccctgtaaac ttaatagttt cacttggatc atatcttatg   2280
accggtcagt tggctggcag tggttaagct agcgctgaag tagcaagaga gagtgtgagg   2340
tagcataggt gtagaattgc tacgtaccag tgtgtgttgc cacccttctt tctgttngct   2400
gccagttagg actaagccaa gaactgcttt cagggatggt tagtgtgagt tct          2453
```

<210> SEQ ID NO 6
<211> LENGTH: 2401

<212> TYPE: DNA
<213> ORGANISM: Artificial sequence
<220> FEATURE:
<223> OTHER INFORMATION: synthetic construct

<400> SEQUENCE: 6

```
agtataaata acaacatgcg atggtgctgc aaagcacact gagtgcaaca aagtgttaac      60
atgaaaggca atgatacact tttgttgcat ttattctaca ctctcttgtt gtttcttgga     120
gtacgaagtt catcttcagc agggaatgga agtaacgatg tcactaaccg taaagaagtt     180
tatatcgtgt atatgggagc cgcagattca acagatgctt ccttccggaa tgaccatgct     240
caggttctca attcagtgct aagaaggaat gagaatgctc tagtacggaa ctacaaacat     300
ggtttctcag ggttcgcagc tcgtctatca aaaaggagg caacctcaat tgctcagaaa      360
cctggtgtgg tgtctgtttt ccctggccca gttctgaaac tccacactac acggtcatgg     420
gatttcctca ataccaaac tcaagtcaaa attgacacca aaccaaatgc ggtctccaaa      480
tcttcttccg tcattggtat cttagacaca ggtatatggc cagaggcggc gagttttagc     540
gacaaggta tgggtcctgt tccatctcgt tggaaaggca cctgcatgaa atcacaagac      600
ttctattcct ccaattgtaa caggaagcta attggcgcaa ggtattatgc tgaccctaat     660
gactcggggg acaacacggc tagggattct aatgggcatg gaacccatgt ggcgggaacg     720
gcagctggtg ttatggtgac taacgcatct tactacggtg ttgcgacagg gtgtgcaaag     780
ggtgggtccc cagagtcaag attagcggtt tacagagtgt gttctaactt tgggtgtcgt     840
gggtcgagca ttcttgctgc gtttgacgat gccattgcgg acggagtgga tttgttgtcg     900
gtgtcactag gtgcatccac tgggtttcga cccgacttga cgtccgatcc gatttcgctt     960
ggagcattcc atgctatgga gcatggcatc ctcgtcgtct gctctgctgg gaacgatgga    1020
cccagctcct acaccctgt caacgatgca ccttggattt taactgttgc agcttccacc     1080
attgatcgaa attttctatc caacatcgtc ttaggtgata caaaatcat caagggcaaa    1140
gctataaatc tatcccctct ttcaaattct cccaagtatc ccctgatata cggtgagtct     1200
gccaaggcga atagcaccag cttagttgaa gcaagacaat gccgcccaaa ttcattagat     1260
gggaataaag tcaaaggaaa gatcgtggtc tgtgatgaca aaaatgataa atattcaact     1320
agaaaaaaag ttgccacggt gaaagcggtg ggaggaattg gtctggttca tattactgac     1380
caaaatgaag caatagcatc aaattatggg gacttcccag caacagtcat aagttcaaaa     1440
gatggcgtca caatcctcca gtacatcaat tcaaccagca atccagtggc aactattcta     1500
gcaacaacat cagttcttga ttataagcct gctcccctgg tgccaaactt ctcatcaaga     1560
gggccttcat cgctttcaag caatattctc aagcctgata ttgcagctcc gggagttaac     1620
attctcgctg catggattgg aaatggcaca gaagtggttc ccaaaggaaa aaagccctca     1680
ctatacaaga taatctcagg gacttccatg gcttgcccgc atgtttcagg gcttgcaagc     1740
agtgtcaaaa cacgcaaccc cgcttggagt gcctcctcaa tcaaatctgc catcatgact     1800
tcagcaattc aaagcaacaa cttgaaggct cccataacaa cggaatcagg gtcggtagcc     1860
acaccttatg actatggagc aggggaaatg acaacatctg aaccattgca accggggcta     1920
gtttatgaaa ccagctccgt tgactacttg aacttcttgt gttacattgg attcaacgta     1980
accacggtta aagtcatctc caaaaccgtc cctcgtaatt tcaattgccc caaggatttg    2040
agctctgatc atatctctaa catcaactac ccttccatag caataaactt cagtggcaaa     2100
agagccgtga acttgagtag aactgttaca aacgttggcg aagatgatga aacagtgtac     2160
```

```
tcccccattg ttgatgctcc cagtggagtg catgtcacat taactccaaa taaacttcgg    2220
tttacgaaaa gtagtaaaaa actaagctac cgagttattt tttcatcaac tctgacctcc    2280
ttgaaggaag atctgtttgg atctattact tggagtaacg gtaagtatat ggttcgaagt    2340 cctttttgtgt taactaagtg aatttaaaag taacgatgaa taaatgcttc ttcatgcttt    2400
t                                                                    2401

<210> SEQ ID NO 7
<211> LENGTH: 1444
<212> TYPE: DNA
<213> ORGANISM: Artificial sequence
<220> FEATURE:
<223> OTHER INFORMATION: synthetic construct

<400> SEQUENCE: 7 caccctcgtgc cggcgactat ggtcgggcag aagttcggcg acaagatcag gtactacgtc     60
cagacggacc cgtcgccaac ggcgaccatc gtgttccgcg gcacagtcat cggcaagtcg    120
ccgtcggcgc ctcgagtggc ggcgttctcg agccgaggcc ccaactaccg cgcaccggag    180
atcctcaagc ccgacgtcat cgccccgggc gtcaacatac tcgcggcgtg gaccggcgcc    240
gcctccccca ccgacctgga catcgactcg aggcgcgtgg agttcaacat catctccggc    300
acgtccatgt cctgcccgca cgtgagcggc ctcgccgcgc tgctccgcca ggcgcacccg    360
gagtggagcc ccgcggcgat caagtcggcg ctcatgacca cggcgtacaa cctggacaac    420
tccggggaaa ccatcaagga cctcgcgacg gcgtgagtt cgacgccgtt cgtccgtggc    480
gccggtcacg tcgaccccaa cgccgccctc gacccagggc tggtgtacga cgccggctcc    540
gacgactatg tcgccttcct ctgcacgctc gggtactctc cgtcgttgat ctccatcttc    600
acgcaggacg catcggtcgc cgactgctcg acgaaattcg ctcgccccgg cgaccttaac    660
taccctgcct tcgccgccgt cttctcctcc taccaagact cggtcaccta ccgccgggtg    720
gtgcgcaacg tcggcagcaa ctccagcgcg gtgtaccagc cgacgatcgc cagcccgtac    780
ggcgtggatg tcacggtgac cccgagcaag ctcgcgttcg acgggaagca gcagagcctg    840
ggatacgaaa tcaccatcgc agtgtcaggc aaccccggtga tcgtggattc cagctactcg    900
ttcggatcca tcacctggag cgacggcgcg cacgacgtca cgagcccat tgccgtgacc    960 tggccgtcca acggtggagc agcagccatg tagtagactg atgctgttgc tactgtctac   1020
cgctgtggga agaaggacag ggccatgagc ccatgagatc cgaaatctcc acgcctcctg   1080
cctgccatag gaataatttc ctcgactgaa ccacgcaata attcagctgc ccctatcgtg   1140
gttgtggtgg accaatggac catgcttgca gctctctctt ttcatttagg ggtaggttgg   1200
ttggagcagc gtatgtgatt ggctgcttgc aaggccgtga gggtgccatc cattatggct   1260
cattggcgat tggacgtgta tgaacaagtt tgtaatgact agaaataatc attgtaccat   1320
gttttttcta tgctggcgcg tttatagcac catgctttgt gtatgtcact tgtgtacgca   1380
tactaaagag aaaagcatgg atatggacca cctgagtgtt cctaaaaaaa aaaaaaaaa    1440 aaaa                                                               1444

<210> SEQ ID NO 8
<211> LENGTH: 1279
<212> TYPE: DNA
<213> ORGANISM: Artificial sequence
<220> FEATURE:
<223> OTHER INFORMATION: synthetic construct

<400> SEQUENCE: 8
```

```
ggagcttcat cttactctca cgacagtttg gcgatagcaa cttttggagc aatggagatg      60 ggtgttttg tctcttgctc agctggcaat ggaggaccag atcctgtcag cctcactaat     120
gtatcaccat ggatcactac agtcggtgct agcaccatgg atagagattt tccaggtagt     180
gttaagctag ggagtgggag aaccatatct ggagtttcac tctacaaagg gcggaggtta     240
ctgcaggcaa acaagcaata ccctcttgtt tatatgggta gtaactcaag cagccctaat     300
ccaagttcat tatgcttaga gggaactttg gatccacatg ttgtttctgg gaaaatcgtg     360
atatgtgatc gaggaataaa tcctaaagtg caaaagggtc aagtagtgaa agatgctgga     420
ggagtaggga tgattttgac aaacactgca gcaaatgggg aggagcttgt tgcaaattgt     480
cacctacttc cagcagttgc agtgggagag atggaaggga agcaatcaa acattatgcc     540 ttaacaaatg ggaaaccaac cgcaactcta gccttttag gtaccagatt gggtgttagg     600
ccatcaccag tggtggcagc attttcatct agaggaccaa atttcctcac acttgaaatt     660
ctcaaacctg atgtggttgc gccagggggtg aacatccttg cagcctggac tggagaattg     720
ggtccgtcaa gtcttccaac agatcatagg agagtgagat caacatatt atcagggact     780 tcaatgtcat gccctcatgt tagtggaatt gctgccttga tcaaggccag acacccagat     840
tggagtgccg cagcagttaa atctgctcta atgacaaccg cttatgttca tgataacatc     900
cataatccac tccaagactc ttccactgca gcagcttcca ctccctatga tcatggagct     960
ggtcatatca acccttttgaa agctctagac ccaggtttga tctatgacat ttcagcccag    1020
gattactttg tattcctctg cacacagaaa ttgactgcaa tacagctaaa agcttttagc    1080
aagcattcca atatgtcttg ccatcacaac acccttgcca ctccaggaga tttgaactac    1140
ccagcaatct cagttgtctt cccagaagat acagccattt caacttttgac tctccataga    1200 acagtcacaa atgttggtcc tctgcttca cattaccatg ttgtagtttc accatttaaa    1260
ggcgtcacca ttaaagttt                                                 1279
```

<210> SEQ ID NO 9
<211> LENGTH: 2566
<212> TYPE: DNA
<213> ORGANISM: Artificial sequence
<220> FEATURE:
<223> OTHER INFORMATION: synthetic construct
<220> FEATURE:
<221> NAME/KEY: misc_feature
<222> LOCATION: (1470)..(1470)
<223> OTHER INFORMATION: n is a, c, g, or t
<220> FEATURE:
<221> NAME/KEY: misc_feature
<222> LOCATION: (1488)..(1488)
<223> OTHER INFORMATION: n is a, c, g, or t

<400> SEQUENCE: 9

```
gaattcggca cgagcagagc ttagagcgcc atgtctgcta ctccttgtgt ttcttctcta      60
ctcatctctg cgattgcagc tgtcgcaagg gctcaaacaa agacgggtat acatcgtcta    120
ccttggggag aggcaacatg aagatgtcag tctcgtcacc tctttgcacc atgacttgct    180
cacttccgtt ctcggaagca aggaggcggc tctcgaatcg attgtccaca gctacagata    240
tggtttctca ggcttttctg caatgcttac tgaatcacaa gcgagaaaga tccagacact    300
gcctggagtg gtgagtgtga aagagaacac aatggtacgc atgcatacta ctcggagctg    360
ggatttcctt gggctgtcca tgggcgtgga catcaagcag gagcagcagc caaatgagct    420
ccttgcagca gcaaaccatg gagatgggat gattatcggt gtcatcgact caggtgtttg    480
```

-continued

```
gcctgagtca cagagcttcg ctgatgatgg ctatggacct cctccttcaa aatggaaggg    540
aacttgccaa gcgggtgcca acttcagtgc ccacgattgc aatcgaaagc tcatcggtgc    600
gcggtggtat gctggccctg acatcgacag gagatttctc caaggtgact tcctgtctgc    660
cagggattct catggccacg gcacccacac agcctccaca gccggtggca acgtcgtcca    720
caacaccagc ttcttcggac tggctgctgg aacggctcgt ggtggcgcac ctcgcgcccg    780
gatagcagtg tacaaggctt gctggggtac ttgctctacc gcgagcgttc tgaaaggcat    840
cgatcatgct atccatgacg gtgttgacgt cctatcgctc tctctcggaa gcacgaacga    900
aatggcagca ctaggaacgc tgggtgcggt ggcaagaggc atcccggtta tcatggcagg    960
cggaaatgat ggacctacag aagaaacggt ggagaattct tcaccatggc tactcacggt   1020
tgctgcaacc atggttgatc gatcattcct cacggttatc accctcgggg ataaccgaca   1080
gtttgtggca caatccatgt atgtggcaga taaaggtgga gatgagttct ctgaacttct   1140
gtattacttt aaggataggt gtgacccgga ctacataaac agcactgaca tacacgggaa   1200
ggtggtattc tgctacacac caggaccggg tagtgtctct gcaccaccca agtatgcaga   1260
tattgcagcg acggtgcaga gaaatggagg gaatggattt atattctcac agaataatct   1320
ggactctctt gatctatatg caattaaagg accggcsctt ccttgcgttc ctctcgactt   1380
caagactagg ctatcagatt gctgtgtact gcaatcgcat tggcatccca aaaataaaga   1440
tatcaacaac ccgaacaacc agcggaagtn aagttgttgc cccaaganta gcagctttct   1500
catcaagggg gcctagtcct atctatcatg gggttctcaa gcctgatatt gctgcacctg   1560
gggtgtacat tttagccgct gcagcacaaa ctggtgctta caaaagtcta ggtgtttcct   1620
atgtcttcga ttctggaaca tccatggcct gcccacatat atctgggata gtcgctctac   1680
tcaaatccgt gcatcctgac tggtcccctg ccgccctaaa atcagcacta atgacaaccg   1740
cacataccat ggacagtcat ggggttccaa tagaagcaaa tggaaatcgt gcaaagatcg   1800
ccgacccgtt tgattacgga gcagggtctg ttaatccaac caaggcagct gatccaggcc   1860
tgatatatga catcagtgcg tcagattacc tcgagttttt caactgtcca caaggatttg   1920
gttcaaataa caattgcaca ccacctgact tgaacctccc atcgattgcc attcctggcc   1980
tcaagacatc tgtgacggtt gtgcgcactg ttaccaatgt tggccagccg aatgcggtgt   2040
acaaggcatt cttggagcct ccacgtgcg tcaagatggc tgtggagcca gcagtgctgg    2100
tgttcagcaa tgcaaggagg gtgcagagtt tcaacgtgac tttcagggcg acccgaagga   2160
tccagggcag ctacaccttc ggtagcttgg catggcatga tggaggcgcc cacctggttc   2220
ggatcccgat tgcagttcgt gtggtgattg aagagctcta ctcagatgcc tcttaagtgg   2280
ggacgttaca tgcagttcga ctgtaaaata aaagacgact ggatctgtat ctgtgttttt   2340
ttttcggaac tcccactatg gctatggtga ttagtgtccg ttcctatggt acgtgaacat   2400
ttatgtcagt gtattgaaaa cttgacataa gtttgtatgg taccggcgga ataaggaaat   2460
ccacccgcaa ctagacaaga ttttctgcct tgctgctagc aatggtaact cccttgatgt   2520
tacaattctt cagactaagt gaatggaaag catcgcatac aacagc               2566
```